United States Patent
Walton

(10) Patent No.: US 7,495,758 B2
(45) Date of Patent: Feb. 24, 2009

(54) APPARATUS AND METHODS FOR TWO-DIMENSIONAL AND THREE-DIMENSIONAL INSPECTION OF A WORKPIECE

(75) Inventor: Steven R. Walton, Buckley, WA (US)

(73) Assignee: Theo Boeing Company, Chicago, IL (US)

( * ) Notice: Subject to any disclaimer, the term of this patent is extended or adjusted under 35 U.S.C. 154(b) by 177 days.

(21) Appl. No.: 11/470,403

(22) Filed: Sep. 6, 2006

(65) Prior Publication Data

US 2008/0055591 A1 Mar. 6, 2008

(51) Int. Cl.
G01N 21/00 (2006.01)
(52) U.S. Cl. .................. 356/237.1; 356/237.3
(58) Field of Classification Search ... 356/237.1–237.5, 356/601, 445–448, 600
See application file for complete search history.

(56) References Cited

U.S. PATENT DOCUMENTS

| 4,846,576 | A | * | 7/1989 | Maruyama et al. ........... 356/604 |
| 5,011,960 | A | * | 4/1991 | Ando et al. .................. 356/608 |
| 5,562,788 | A | | 10/1996 | Kitson et al. |
| 6,118,540 | A | * | 9/2000 | Roy et al. .................... 356/394 |
| 6,400,849 | B1 | | 6/2002 | Lee et al. |
| 6,462,813 | B1 | * | 10/2002 | Haven et al. .............. 356/237.2 |
| 2004/0257540 | A1 | | 12/2004 | Roy et al. |
| 2005/0025350 | A1 | | 2/2005 | Engelbart et al. |
| 2005/0116952 | A1 | | 6/2005 | Je et al. |
| 2007/0271064 | A1 | * | 11/2007 | Walton ...................... 702/158 |
| 2007/0280501 | A1 | * | 12/2007 | Walton ...................... 382/100 |

FOREIGN PATENT DOCUMENTS

| JP | 7-71931 | 3/1995 |
| WO | WO 00/70303 | 11/2000 |

OTHER PUBLICATIONS

International Search Report and Written Opinion for International Appl. No. PCT/US2007/016175, mailed Jan. 2, 2008.
U.S. Appl. No. 11/202,411, Engelbart et al.
U.S. Appl. No. 11/383,681, Savol et al.
U.S. Appl. No. 11/421,273, Walton.
Asla M. Sa, Paulo Cezar Carvalho, and Luiz Velho; *Recovering Registered Geometry and High Dynamic Range Texture with Coded Structure Light*; pp. 1-4. Printed from website http://www.wscg.zcu.cz/wscg2003/Papers_2003/E03.pdf. (2003).

(Continued)

Primary Examiner—Hoa Q Pham
(74) Attorney, Agent, or Firm—Alston & Bird LLP

(57) ABSTRACT

Apparatus and methods for inspecting a workpiece are provided. According to one embodiment, a method for inspecting a workpiece comprises illuminating at least a portion of the workpiece with at least one illumination beam and capturing at least one image including at least on line signature formed by illuminating the workpiece with the illumination beam. The method further includes performing two-dimensional and three-dimensional processes on the captured image and classifying at least one feature associated with the workpiece based at least in part on data generated by the two-dimensional and three-dimensional processes.

31 Claims, 12 Drawing Sheets

OTHER PUBLICATIONS

Li Zhang, Brian Curless, and Steven M. Seitz, Department of Computer Science and Engineering, University of Washington;*Rapid Shape Acquisition Using Color Structured Light and Multi-pass Dynamic Programming*; pp. 1-13; 13 pages printed from website http://www.grail.cs.washington.edu/projects/moscan/paper.pdf on Mar. 27, 2006.

Asla M. Sa, Paulo Cezar Carvalho, and Luiz Velho;-*BCSL: Structured Light Color Boundary Coding for 3D Photography*; VMV 2002; pp. 1-9; Erlangen, Germany, Nov. 20-22, 2002. Printed from website http://www.visgraf.impa.br/Data/RefBib/PS_PDF/vmv02/bs-BCSL.pdf.

*3D Images Using Color Structured Light*; Way-2C Color Machine Vision—3D Images Using Color Structured Light; 2 pages printed from website http://www.way2c.com/w2csl.htm on Mar. 27, 2006.

* cited by examiner

APPARATUS AND METHODS FOR TWO-DIMENSIONAL AND THREE-DIMENSIONAL INSPECTION OF A WORKPIECE

BACKGROUND OF THE INVENTION

1) Field of the Invention

Embodiments of the present invention relate to the inspection of a workpiece and, more particularly, to apparatus and methods for providing two-dimensional and three-dimensional information indicative of a workpiece.

2) Description of Related Art

Composite structures are commonly manufactured by progressively building up the structure with a plurality of layers of thin composite tape (or tow) laid one layer upon another. Typically, the operation begins by laying one or more tapes onto a starting template or tool that has a configuration generally corresponding to the desired shape of the article to be produced. A tape placement head of a manufacturing system moves over the surface of the template, guiding the one or more tapes of composite material onto the template. The head usually makes repeated passes over the template in a defined pattern until the composite material is entirely collated, building up successive layers of the composite tape to form the desired workpiece. A compaction roller is typically used for pressing the tape against the workpiece, thereby facilitating adhesion of the successive layers. The workpiece may then be subjected to a curing process (e.g., heating) to further adhere and bond the composite layers. Conventional systems for forming composite structures using successive layers of tape include those systems disclosed, for example, in U.S. Pat. No. 6,799,619 issued to Holmes et al. and U.S. Pat. No. 6,871,684 issued to Engelbart et al.

The measurement accuracy required by the manufacturing specification, which is in turn driven by design requirements, in areas such as ply boundaries, tape edge gaps and overlaps, material wrinkles, and the presence of foreign object debris (FOD), has created a need to make those measurements with a robust automated system. Prior and emerging art, using various machine vision technologies, have provided limited capabilities to meet these requirements. As such, manual visual inspection of composite plies is frequently employed, which may be unreliable, inefficient, and subject to operator error. Namely, the machine must be stopped and the process of laying materials halted until the inspection is complete. During the inspection, the operator verifies the dimensions of any suspect inconsistencies and quantifies the number of inconsistencies per given unit area. The inconsistencies are repaired as needed and laying of the next ply proceeds.

Vision systems have been developed that are capable of inspecting workpieces as tape is laid thereon. Typically, a laser projector is employed that generates a laser signature on the workpiece, while a camera is used to capture an image of the workpiece that includes the laser signature illuminated thereon. The original presumption was that the expected laser line signatures seen during normal manufacturing would be well-known, and any variance from a "perfect" signature constituted a detected inconsistency. Thus, operation of the camera required reasonably clean, straight laser signatures in a particular location in the image frame. This assumption proved unworkable in the real world once prototype systems were built and tested on an actual composite tape lay-up machine.

For instance, the optical appearance of the composite materials may not be as consistent as obtained from coupons that have been examined earlier in the laboratory and vary greatly in reflectivity degree and sensitivity to fiber orientation. In addition, the working distance from the camera to the workpiece varies significantly, which causes the laser signature to move completely through the vertical extent of the camera frame, rather than remaining near the centerline of the image height. The large motion of the workpiece also moves the surface outside of the focal depth of fields of both the laser projector and the camera. While the camera's depth of field is easily controlled by modifying the lens, the depth of field of the laser generator cannot be changed such that the imaged laser signature is often out of focus. Moreover, the actual working depth of field is at times transited at very high velocity (i.e., there are sharp "bumps" in the surface of the workpiece in addition to slowly-changed "swells"), which produces significant motion blur in the vertical image direction as the laser signature sweeps through the field. The surface of the workpiece is not always flat, resulting in laser signatures that are rarely straight lines. Furthermore, methods of FOD detection and classification that depend upon two-dimensional machine vision algorithms are defeated by the presence of a strong laser line signature.

It would therefore be advantageous to provide apparatus and methods for inspecting a workpiece to increase the reliability and accuracy of the inspection of the workpiece. In addition, it would be advantageous to provide apparatus and methods to increase the quality of a workpiece, the production rate, and inspection efficiency, as well as reduce the overall cost of the manufacturing and inspection processes.

BRIEF SUMMARY OF THE INVENTION

Embodiments of the invention may address at least some of the above needs and achieve other advantages by providing apparatus and methods for inspecting a workpiece. Generally, embodiments of the present invention include apparatus and methods for interpreting images of a workpiece in order to characterize a feature identified on the workpiece. In particular, embodiments provide apparatus and methods for generating information indicative of the workpiece based on one or more images captured by a camera, wherein the images are generated in response to the illumination of the workpiece with one or more illumination sources. For instance, apparatus and methods of the present invention could be used to provide both two-dimensional and three-dimensional information indicative of the workpiece, analyze the illuminated portion of the workpiece despite the presence of noise, and locate and classify various features associated with the workpiece.

In one embodiment of the present invention, a method for inspecting a workpiece is provided. The method includes illuminating at least a portion of the workpiece with at least one illumination beam, such as at an oblique incidence angle relative to the workpiece, and capturing at least one image including at least one line signature formed by illuminating the workpiece with the illumination beam. The method may include performing a manufacturing process on a moving workpiece during the illuminating and capturing steps. The method further includes performing two-dimensional and three-dimensional processes on the captured image and classifying at least one feature associated with the workpiece (e.g., foreign object debris) based at least in part on data generated by the two-dimensional and three-dimensional processes.

According to various aspects of the method, the capturing step includes capturing at least one image comprising at least a background and the line signature illuminated on the workpiece. The method may also include isolating the line signature from the background captured on the image, generating a power histogram of the background and line signature, and/or determining a vertical location of the line signature based on the power histogram. In addition, performing the two-dimensional processes may include calculating at least one of an image background power, a background image noise power, and a power ratio of the line signature to the background.

Additional aspects of the method include identifying bright and dark contiguous objects on the captured image using an intensity threshold level. Performing two-dimensional processes may include determining at least one of size, shape, total power, and location of each of the bright and dark contiguous objects, while performing three-dimensional processes may include disassociating the bright and dark contiguous objects associated with the line signature from those bright and dark contiguous objects not associated with the line signature. Moreover, performing three-dimensional processes may include determining a location of a centerline of each line signature and an extent of each column representative of the disassociated bright and dark contiguous objects. The three-dimensional processes may further include extrapolating an aggregate centerline representative of a centerline of the line signature based on each of the centerlines determined for each of the disassociated bright and dark contiguous objects, as well as convolving the aggregate centerline with a step filter kernel. The three-dimensional processes may then locate peaks provided by the step filter kernel.

An additional embodiment of the present invention provides a method for inspecting a workpiece. The method includes illuminating at least a portion of the workpiece with at least one illumination beam and capturing at least one image comprising at least one line signature formed by illuminating the workpiece with the illumination beam. The method further includes performing three-dimensional processes on the captured image, wherein the three-dimensional processes comprise determining at least one of a location of each line signature and an extent of at least a portion of each line signature, and providing information indicative of at least one feature associated with the workpiece based on data generated by the three-dimensional processes. For example, information indicative of respective edges of the workpiece, a gap in the workpiece, an overlap on the workpiece, and/or a foreign object debris associated with the workpiece may be provided.

Variations of the method include identifying bright and dark contiguous objects on the captured image using an intensity threshold level. The three-dimensional processes may include disassociating the bright and dark contiguous objects associated with the line signature from those bright and dark contiguous objects not associated with the line signature. Furthermore, the three-dimensional processes may comprise determining a vertical location of a centerline of each line signature and a vertical extent of each column representative of the disassociated bright and dark contiguous objects, as well as extrapolating an aggregate centerline representative of a centerline of the line signature based on each of the centerlines determined for each of the disassociated bright and dark contiguous objects. In addition, the three-dimensional processes could include convolving the aggregate centerline with a step filter kernel and then locating peaks provided by the step filter kernel.

Further variations of the method include identifying a gap, an overlap, a double step up, and/or a double step down on the workpiece based at least in part on the number of peaks located by the step filter kernel. The method may further include determining a width between a pair of peaks provided by the step filter kernel for each identified gap or overlap and/or calculating a low spatial frequency surface and/or a high spatial frequency surface associated with the workpiece based at least in part on data generated by the three-dimensional process. In addition, the method may include detecting at least one feature associated with the workpiece based at least in part on the low spatial frequency surface, the high spatial frequency surface, and/or the data generated by the three-dimensional process.

A further aspect of the present invention provides an apparatus for inspecting a workpiece. The apparatus includes at least one illumination source positioned proximate to the workpiece and configured for illuminating at least a portion of the workpiece with at least one illumination beam. The apparatus also includes at least one camera positioned proximate to the workpiece and configured for capturing at least one image comprising at least one line signature formed by illuminating the workpiece with the illumination beam. Moreover, the apparatus includes a data system capable of performing two-dimensional and three-dimensional processes on the captured image and classifying at least one feature associated with the workpiece based at least in part on data generated by the two-dimensional and three-dimensional processes.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Figure 1:
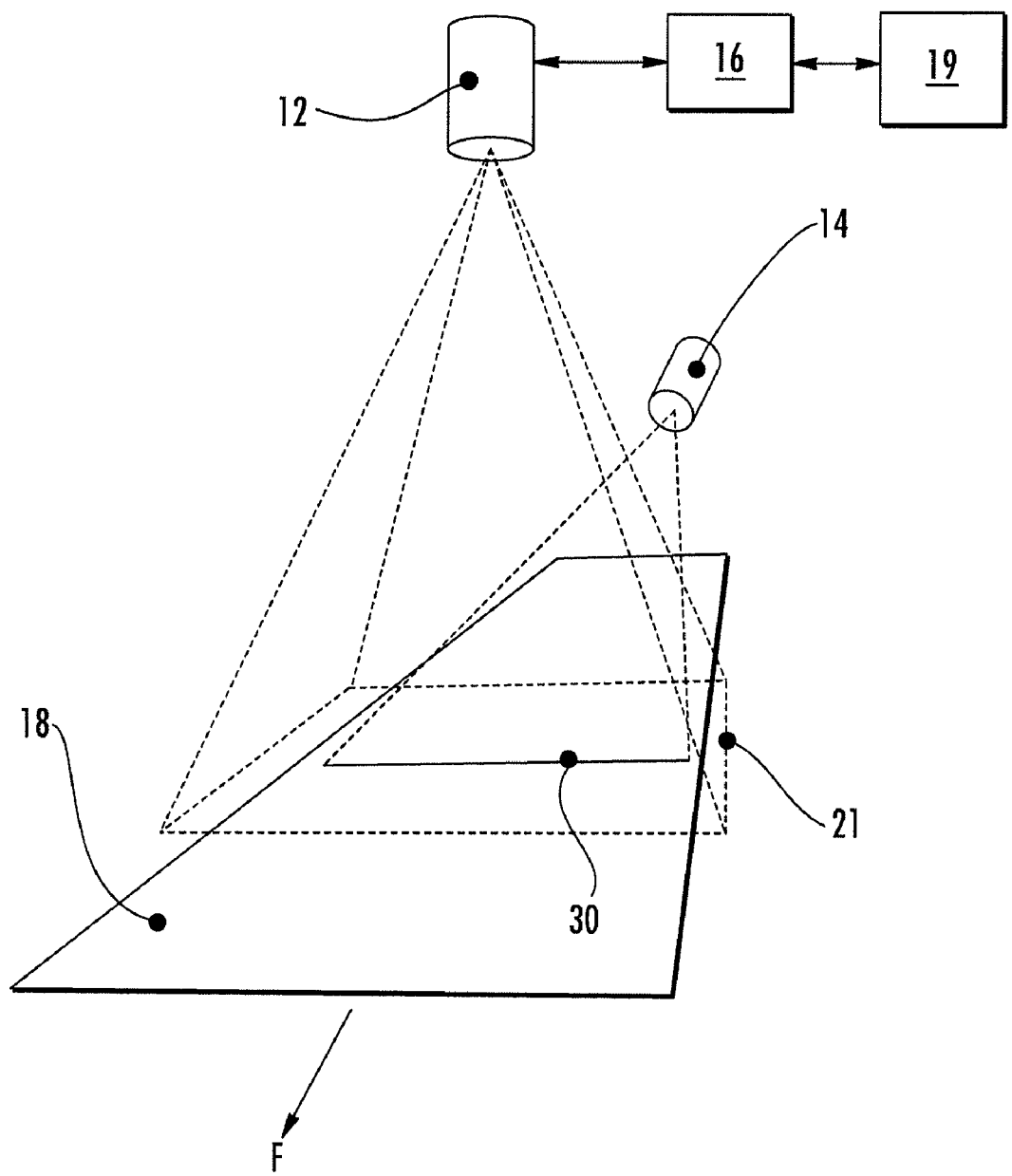
FIG. 1 is a perspective view of an inspection system according to one embodiment of the present invention.

Referring now to the drawings and, in particular to FIG. 1, there is shown an inspection system 10 for identifying and locating features in a workpiece. The system 10 includes a camera 12 and at least one illumination source 14, in some combination determined by the type of workpiece to be inspected, that acquire data indicative of the workpiece 18. The camera 12 and illumination source 14 are in communication with a data system 16 such that the data system may provide and/or process data captured by the camera. For example, the data system 16 could provide characteristic information of a feature captured by the camera 12. As will be explained in further detail below, the inspection system 10 utilizes both two-dimensional (2D) and three-dimensional (3D) information in conjunction with in-process inspection such that more efficient and reliable detection and characterization of features in the workpiece 18 are provided.

The information indicative of features associated with the workpiece 18 is used to classify (identify) the presence or absence of the features in the camera's 12 image frame, using both general mathematical techniques and specific methods suggested by the nature of the workpiece being inspected, after which the importance of the particular set of features is weighted and/or selected to perform a further measurement of extent and type using other algorithms derived from empirical experience with the use of the system on a large range of actual workpieces. The information may then be compared with specifications for the particular portion of the workpiece 18 to generate out-of-specification indicators for later correction or for use in conjunction with various methods of indicating features and locations of features to an executive controller 19. As such, the executive controller 19 is responsible for using the information from the algorithms to determine a course of action, such as repair or replacement of the workpiece. Thus, the executive controller 19 could be a human operator for analyzing the data and/or a data system capable of processing the information.

The term "feature," as used herein, is not meant to be limiting, as a feature could be any aspect, discontinuity, imperfection, or inconsistency in the workpiece that may require attention by an executive controller 19, such as for repair or replacement of the workpiece or a portion of the workpiece. For example, an inconsistency could be a material wrinkle or foreign object debris ("FOD"), such as paper, plastic sheet, resin balls, carbon fiber "fuzzballs," or other material inimical to the production of composite parts. Moreover, the system 10 can detect the presence of features associated with the workpiece that would not ordinarily be characterized as an inconsistency, such as a ply boundary, topology, shape/contour, or a tape edge gap or overlap, the positioning of which are requirements of the engineered workpiece design specification.

The inspection system 10 could be used to inspect any number of workpieces in a variety of industries where detection of features of the workpiece is required or desired, such as in the aircraft, automotive, or construction industries. Thus, the term "workpiece" is also not meant to be limiting, as the inspection system 10 could be used to inspect any number of parts or structures of different shapes and sizes, such as machined forgings, castings, or panels. For instance, the inspection could be performed on newly manufactured workpieces or existing workpieces that are being inspected for preventative maintenance purposes. Further, the workpiece could be any number of composite, plastic, and/or metallic materials.

Moreover, the system 10 could be used during the assembly or processing of the workpiece (e.g., as composite tape is being laid upon a mandrel), as well as before or after assembly for providing information characteristic of the workpiece. For example, the system 10 could be utilized during the manufacture of aircraft wing skins or stringers, such as in conjunction with a lamination machine for laying onto a workpiece composite tape (typically 1" or wider material) or tow (typically less than 1" in width) plies of varying shapes. Differing width material may be applied to a given ply, depending upon engineering requirements. A lamination machine, as known to those skilled in the art, is a device for laying this resin-impregnated carbon fiber material onto a mandrel to form a workpiece and can have various configurations. For instance, the lamination machine could include a gantry and a plurality of tape heads for laying down tape of composite material. The gantry is capable of translating so that tape is laid as the mandrel rotates and as the gantry translates longitudinally. However, although the system 10 is discussed herein in conjunction with a lamination machine for laying composite tape or tow plies onto a workpiece, the system could be employed to inspect various workpieces during various processes. The system 10 can be mounted onto a moving lamination head, a separate moving gantry, or statically on any portion of the machine that has appropriate access to the workpiece, and may be enabled, disabled, or dynamically reconfigured according to the requirements of a particular manufacturing process.

The inspection system 10 could also be used in conjunction with an image-projecting device. The image-projecting device could be any device capable of projecting a visible image onto the workpiece. For instance, the image-projecting device could be a laser projector or a digital projector capable of projecting an image indicative of a feature captured by the camera 12 such that the location of the feature can be readily identified. In addition, the image-projecting device could project images for facilitating the manufacture of the workpiece, such as a template for locating laminate plies during lay up of the composite tape. An exemplary projection system is disclosed in U.S. patent application Ser. No. 11/293,443, entitled "System for Projecting Flaws and Inspection Locations and Associated Method," which is assigned to the present assignee and incorporated herein by reference.

As described above, the camera 12 and illumination source 14 are employed to inspect a workpiece and communicate with a data system 16. In many cases, communications cable(s) of wire or optical fiber transmit data between the camera 12 and the data system 16. In other embodiments, the data may be transmitted between the camera 12 and the data system 16 via wireless communications. The camera 12 may be directly connected to the data system 16, or indirectly connected, such as via a network. In further embodiments of the present invention the data system 16 may be located proximate to the camera 12, such that remote connections between the camera and data acquisition system are not necessary.

The data system 16 could include a processor or similar computing device operating under the control of imaging software so that any features in the workpiece may be characterized. Although the data system 16 may process the data upon receipt, the data system may also include a memory device for storing the data, such as for subsequent review and analysis by an executive controller 19. Thus, the data system 16 could simply be a database for storing location information and/or data indicative of a feature, such that the information may accessed at a later time and processed by the same data system or another data system for characterizing features in the workpiece. The data system 16 is capable of generating data and/or images indicative of a feature of the workpiece and may also allow a user to store and edit previously generated data and/or images, such as in the memory device. However, it is understood that the data system 16 need not generate images, as the data system could mathematically collect and analyze data and generate, for example, location information of various workpiece features in terms of coordinates or the like.

In particular embodiments, the data system 16 is configured to display images representing data captured by the camera 12 in real time such that a real-time video display of the captured data may be shown. Also, in particular embodiments, the data system 16 is configured to allow a user to capture one or more still images of the data and, for example, to display the still images on a display screen or print the images. However, it should also be understood that the camera 12 may be adapted to capture images at pre-determined times and then to send the images to the data system 16 for display by a graphical interface or for output by an output device, such as a printer.

It is further understood that each camera 12 may include an associated data system 16, while each data system may, in turn, be in communication with a central data system. Thus, a central data system in such a tiered architecture could collect and/or further analyze images captured by respective cameras 12 and/or images or other data provided by respective data systems 16. In addition, the data system 16 includes a processor or other computing device that may be adapted to execute one or more applications (e.g., programs) and to otherwise operate under control of a standard operating system. For instance, the data system 16 may employ various software programs for processing and displaying the images captured by the camera 12. As will be explained in further detail below, the data system 16 and, more particularly, the software programs executed by the data system can employ various algorithms for analyzing and interpreting the images captured by the camera 12. Typically, the operating system and the various applications, e.g., software programs, are stored in the memory device or are otherwise accessible to the processor or other computing device. These algorithms are employed to reduce computational overhead and arranged to enable the use of multiprocessing to maximize the use of resources of the data system 16, up to and including a "distributed processing model" using peer-to-peer network of standard computers.

The camera 12 may be any suitable camera or other image capturing device capable of capturing data indicative of the workpiece such that the data system 16 can process the data and determine whether a feature is present and/or provide information indicative of various features associated with the workpiece 18. In particular, the camera 12 typically captures images of the workpiece, and the data system 16 processes the images. The camera 12 is positioned to capture images generally overhead and with its optical axis aligned perpendicular to the workpiece 18, although the camera could be located at other positions and/or orientations if desired, such as in instances in which the surface of the workpiece is non-planar or where a particular feature desired to be detected requires or is best imaged with a particular orientation of the camera. The inspection system 10 may include one or more cameras 12, such as a respective camera for each tape laying head. The camera 12 may be a commercially-available camera capable of acquiring color images, not necessarily limited to the visible spectrum of light. For example, in one embodiment, the camera 12 is a television or other type of video camera, an infrared-sensitive camera, a visible light camera with infrared-pass filtration, a fiber optic camera, a coaxial camera, a monochrome camera, a Charge Coupled Device (CCD), or a Complementary Metal Oxide Sensor (CMOS). The camera 12 may also include an imager and a lens (see FIG. 2) and filter systems or the like in which one or more specific frequencies of light are recorded. The camera 12 can be positioned proximate the workpiece on a stand or mounted to a frame or similar device. For instance, the camera 12 could be carried proximate to a tape laying head on a lamination machine and translate along with a gantry.

Figure 2:
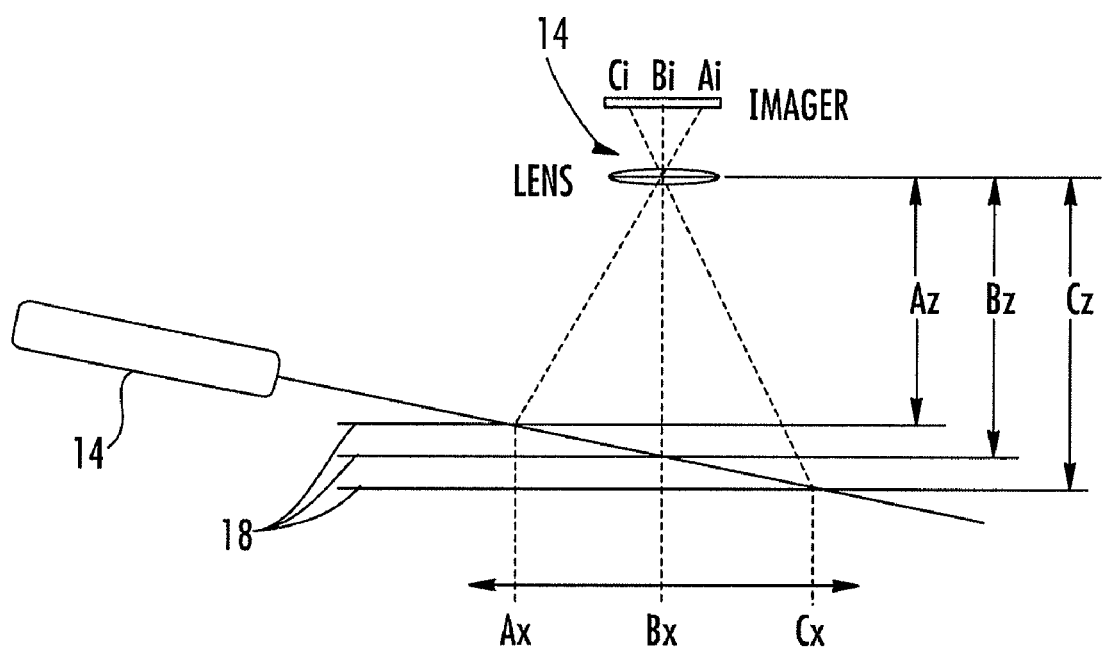
FIG. 2 is an elevation view of the inspection system shown in FIG. 1.

As demonstrated in FIG. 1, the camera 12 is oriented such that the image of the laser signature 30 is aligned from left to right across the camera's field of view 21. If the surface of the workpiece 18 is a plane, the laser signature 30 is a simple straight line. As the workpiece 18 moves closer or further away from the camera 12, the laser signature 30 moves correspondingly up and down in the image. For instance, FIG. 2 illustrates that as the workpiece 18 moves down through positions Az, Bz, and Cz, the laser line signature 30 moves along the workpiece through Ax, Bx, and Cx, which moves the position of the bright line through locations Ai, Bi, and Ci on the camera image.

The illumination source 14 typically includes a laser generator or LED array such that the illumination source is any device capable of illuminating the workpiece 18 with an illumination beam, such as a planar fan beam or shaped light wash to form a laser signature 30 on the workpiece. As shown in FIG. 1, the illumination source 14 is a laser generator that is capable of illuminating a workpiece 18 with a fan beam to form a laser signature 30 on the workpiece. The illustrated embodiment depicts a shallow-incidence fan beam (i.e., an angular section of a plane, wherein light "fans" out from an illumination source 14 that is spread in one dimension by optical means) observed from above by a camera 12 with an optical axis perpendicular to the workpiece 18. A laser "signature" is formed on the surface of the workpiece 18 by the intersection of the planar fan beam and the topology of the workpiece.

A planar fan beam may be oriented by rotating around its optical axis such that the fan produces a line (i.e., a laser signature) on the workpiece perpendicular to the optical axis of the laser generator, in the plane perpendicular to the workpiece described by the incidence angle of the laser generator, or at any angle in between. The pitch or roll angle of the illumination source 14 could also be varied to change the incidence angle of a respective illumination beam on the workpiece 18. Thus, the laser generator could be a laser projector, a laser scanner, or the like capable of illuminating the workpiece 18 with a fan beam. The fan beam is generally a beam of light that spans outwardly in a plane from its origin location. Each LED array, as known to those of ordinary skill in the art, is generally an arrangement of bulbs for generating a light wash, such as a beam of light or other structured light that is configured to illuminate a specific feature on the workpiece 18. Each illumination source 14 is capable of illuminating the workpiece 18 with structured light having a particular color (e.g., red, blue, and green) or additional specific spectral content.

Each illumination source 14 is configured in a specific geometric location and pointing direction depending on the type of feature desired to be detected. Additionally, an LED array may be of a specific shape to enhance particular features present in the workpiece. As shown in the embodiment illustrated by FIG. 1, the laser generator 14 is positioned to illuminate the workpiece 18 at an oblique incidence angle, where the incidence angle is an angle measured between a line drawn parallel to the workpiece and the fan beam. The ability of the system 10 to resolve vertical changes in topology (e.g., a gap between adjacent tape courses that exposes the underlying ply layer) is inversely proportional to the total working depth of field (e.g., required if the workpiece moves significantly in the vertical direction with respect to the camera as the workpiece is inspected). The sensitivity of this relationship is determined by the incidence angle of the fan beam with respect to the surface. According to one aspect of the present invention, the incidence angle is shallow (e.g., less than about 30°). A range of incidence angles from approximately 5° to 30° may be employed in order to match the required measurement accuracy of tape laps and gaps to the desired vertical depth of field of the embodiment, and to generate more data indicative of surface debris in order to separate actual tape edges from common ridge-like structures in central regions of the workpiece 18. The edges of the workpiece 18 are generally parallel with the direction of movement of the workpiece (shown as direction of arrow F) during processing. The laser generator 14 is capable of generating a fan beam configured as a laser signature 30 on the workpiece 18 that is perpendicular to the direction of the workpiece.

It is understood that the number and configuration of the camera 12 and illumination source 14 shown in FIG. 1 are not meant to be limiting. In this regard, there may be any number of laser generators and/or LED arrays arranged in particular geometric configurations depending on the type of workpiece 18 being inspected and/or the features desired to be detected. For example, U.S. patent application Ser. No. 11/421,273, entitled Method and System for Two-Dimensional and Three-Dimensional Inspection of a Workpiece, and U.S. patent application Ser. No. 11/383,681, entitled Systems and Methods for Monitoring Automated Composite Fabrication Processes, which are incorporated herein by reference, provide various configurations of inspection systems utilizing one or more illumination sources and a camera. In addition, there may be one or more cameras 12 utilized depending on the area of the workpiece 18 to be inspected, as well as various other factors, such as the desired speed or accuracy of inspection. Furthermore, and as indicated above, the workpiece 18 may be various sizes and configurations and include features associated with the workpiece that are not limited to identifying features associated with workpieces comprising composite tape. For example, the system 10 is capable of providing information regarding various features associated with a workpiece 18, such as respective edges of a workpiece, a topology of the workpiece, a shape of the workpiece, and an inconsistency in the workpiece (e.g., presence or location of the inconsistency). With respect to composite workpieces 18, the system 10 is further capable of providing information indicative of respective edges of a tape ply, an end-of-tape condition, presence of absence of specific tows within a course, twists or displacements of tows, a gap between tape plies, a topology of a tape ply, a wrinkle, pucker, or tear in a tape ply, and/or an inconsistency in a tape ply (e.g., FOD including paper, plastic sheet, resin balls, carbon fiber, "fuzzballs"), or other material inimical to the production of composite workpieces.

The laser line signature 30 depicts a narrow slice of the image. As will be described in further detail below, algorithms analyze the laser signature 30 generated by the illumination source 14 that may be unfocused or "fuzzy." In these algorithms, the data system 16 uses knowledge of the laser fan beam's or LED light wash's color, shape, and source location and direction. The data system 16 thus may provide 2D (any information other than that resulting from illumination of the workpiece by means of a laser fan beam) and 3D (information associated with the illumination of the workpiece by means of the laser fan beam) measurement of any features associated with the workpiece 18 such that these features may be identified in order to, for example, repair the workpiece, facilitate further processing of the workpiece, or provide a location for projection of inconsistency type and location onto the workpiece. Thus, 2D information may relate to the information captured by a camera from the perspective of a plan view, while 3D information (e.g., depth) may relate to information captured by the camera associated with the illumination beam illuminated on the workpiece at a desired incidence angle. For instance, the data system 16 could provide the width and height of a gap in a workpiece 18, as well as the specific location of a feature of the workpiece. According to one embodiment, encoders could be employed to provide positional information for locating features identified during the inspection process. For example, a composite tape lamination machine could utilize encoders on tape laying heads and/or the gantry to provide positional information that could be correlated with the images obtained by the camera 12. In addition, or alternatively, the system can utilize a common time base (precision clock) to tag all outputs such that the location of detected features can be derived by correlating with time-tagged machine head and/or gantry locations recorded by a separate machine control system.

The overall operation of the algorithms described herein in conjunction with FIGS. 4-9 generally involves static calibration (i.e., before operation of the camera), dynamic calibration (on an image frame-by-frame basis), extraction of numerous characteristics from each image, and analysis of these characteristics for the purpose of generating 2D and 3D information for reporting to an external executive controller 19 concerning the features discovered on the workpiece.

Figure 3:
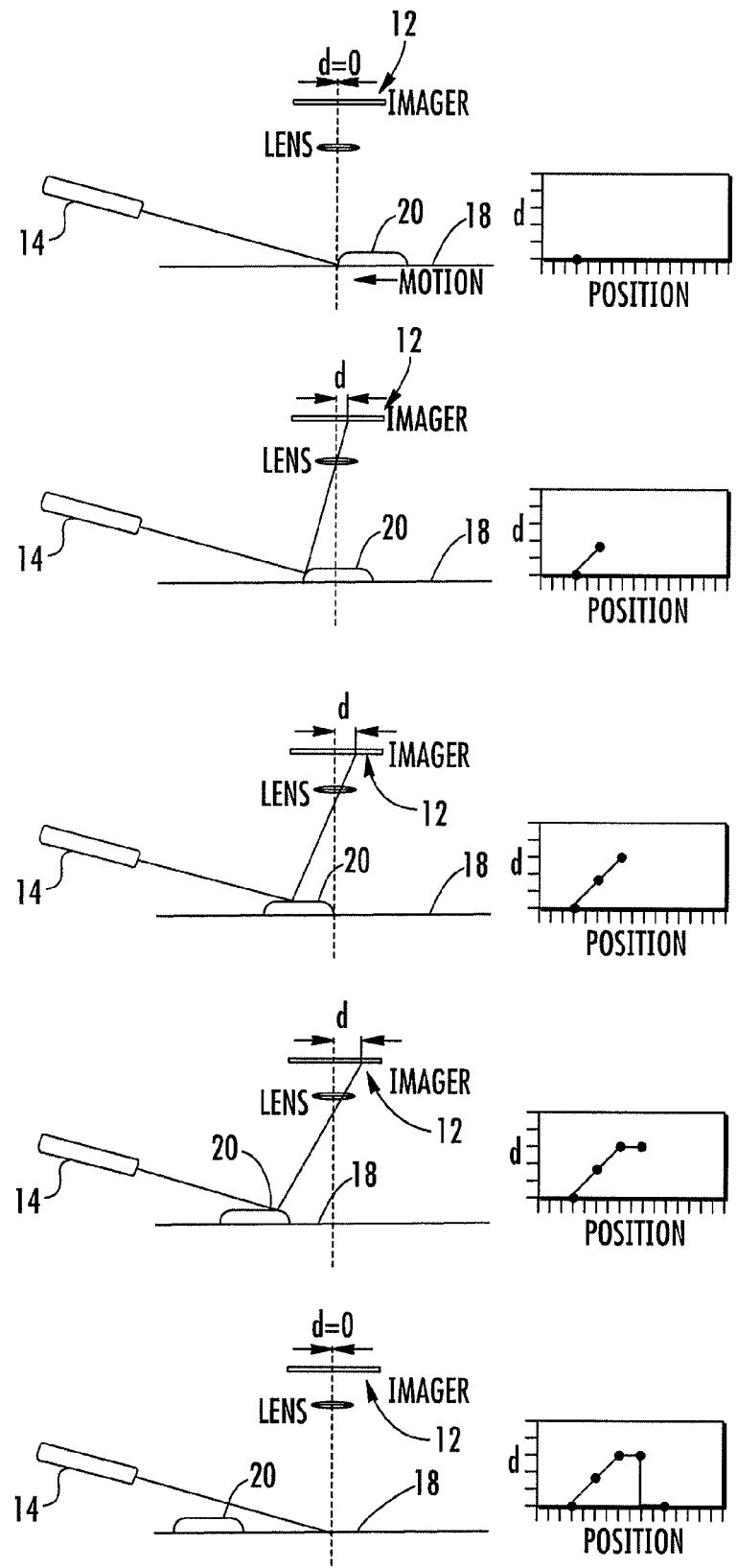
FIG. 3 illustrates a plurality of images to generate a pseudo three-dimensional topology of a feature according to one embodiment of the present invention.

As used herein, algorithms for inspecting a workpiece according to one embodiment of the present invention are capable of generating 2D and 3D information indicative of features associated with the workpiece. Although the position of the illumination beam responds to 3D topology, the illumination beam is not a continuous surface, nor is the apparent shape an exact analog of a depth field. Thus, the trailing portions of protruding objects may cause a region to be "shadowed," such that the trailing portions are not illuminated by the illumination beam, if the surface tangent is a steeper angle than the incidence of the illumination beam. Also, a "rising" surface will respond more slowly than a "falling" surface. FIG. 3 illustrates a small symmetric surface feature 20 that moves from right to left beneath a camera 12. As the feature 20 is moved from right to left in FIG. 3, the illumination source 14 projects an illumination beam on the leading edge and top surface of the feature, but is incapable of projecting onto the trailing edge of the feature due to the angle of incidence of the beam. Thus, there is a sharp drop in the position of the trailing edge of the feature 20 because portions of the trailing edge are not illuminated. This projective distortion of apparent shape primarily occurs in the travel direction of the feature 20, and only to a limited extent in the lateral direction (i.e., 90 degrees from the travel direction) because the illumination source 14 projects an illumination beam from a point aperture rather than a true sheet of collimated light.

Figure 11:
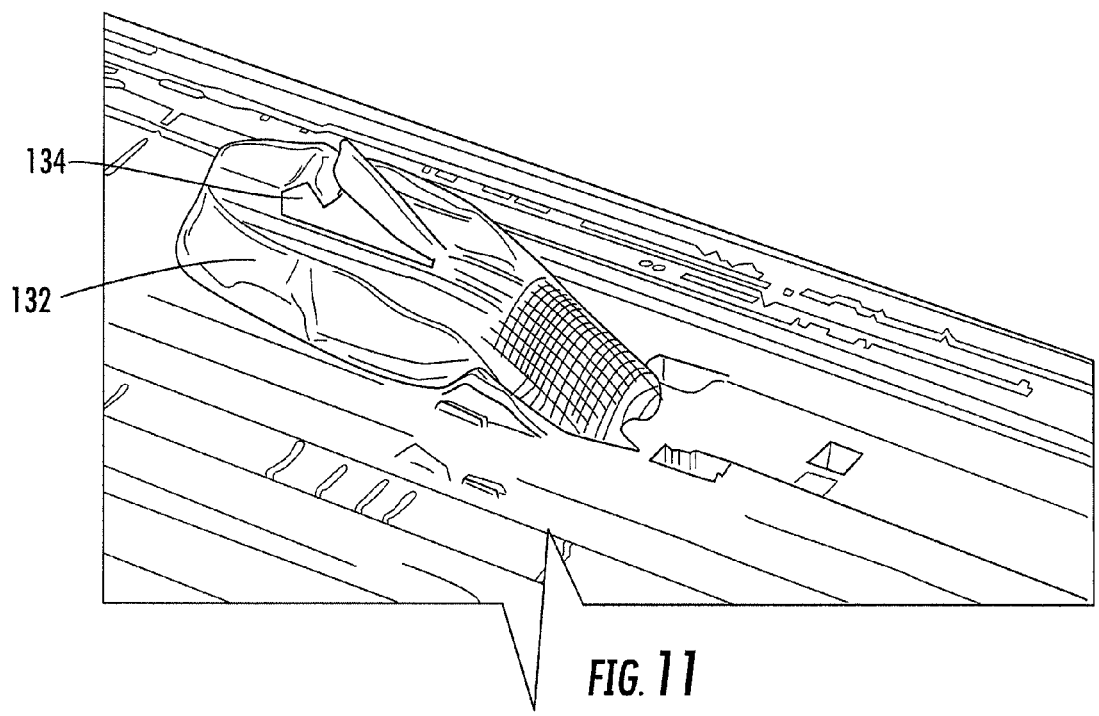

The effect that has been described herein as "pseudo-3D" is not very evident when the workpiece topology changes primarily in a direction lateral to the direction of sensor travel, as shown in FIG. 11. However, if the actual FOD object has any significant height it becomes quite evident. FIG. 11 depicts a common machine screw flat washer 132 that is scanned over by the camera. The exaggerated approached edge is clearly illustrated (see FIG. 3 for a 2D slice of this effect), and there are spurious peaks 134 around the center hole of the washer, which are caused by the bright glints of scratches in the metal. Spurious peaks caused by bright glints in the material are typically not generated with respect to composite materials because inconsistencies such as the presence of washers are typically not encountered.

Therefore, for certain size-measurement algorithms, a "pseudo" 3D surface is built in the camera memory by "stacking" laser signatures adjacent to one another as the camera is moved along a stationary workpiece, or, alternately, the workpiece is moved under a stationary camera. Although the surface of the workpiece appears to be continuous, thus simplifying aspects of the detection and classification algorithms, in reality the actual workpiece shape is not measured completely (due to shadowing) unless there are no surface regions with tangents greater than the incidence angle of the illumination beam. However, for the application of composite layups of various types, the advantages of the depth sensitivity gained by using a shallow-angle laser outweighs the disadvantage of possibility of confusion due to high-tangent surface regions, because such typically do not occur in these processes.

Moreover, in the context of composite tape and tow layup on a flat mandrel, the laser line signatures are processed without first triangulating their positions to true 3D locations in space. The vertical locations of the signatures in the camera frame are used directly, such that any "topological" information recovered on a per-frame basis is actually within the plane of the illumination beam illuminated on the workpiece. Thus the laser signature should not be understood as a vertical slice of the workpiece, but rather as a slice of the surface in the illumination plane itself. These slices occur at the frame rate of the camera; thus, a slowly-moving workpiece (or camera) samples the surface densely, and a fast-moving workpiece (or camera) samples the surface sparsely.

Figure 4:
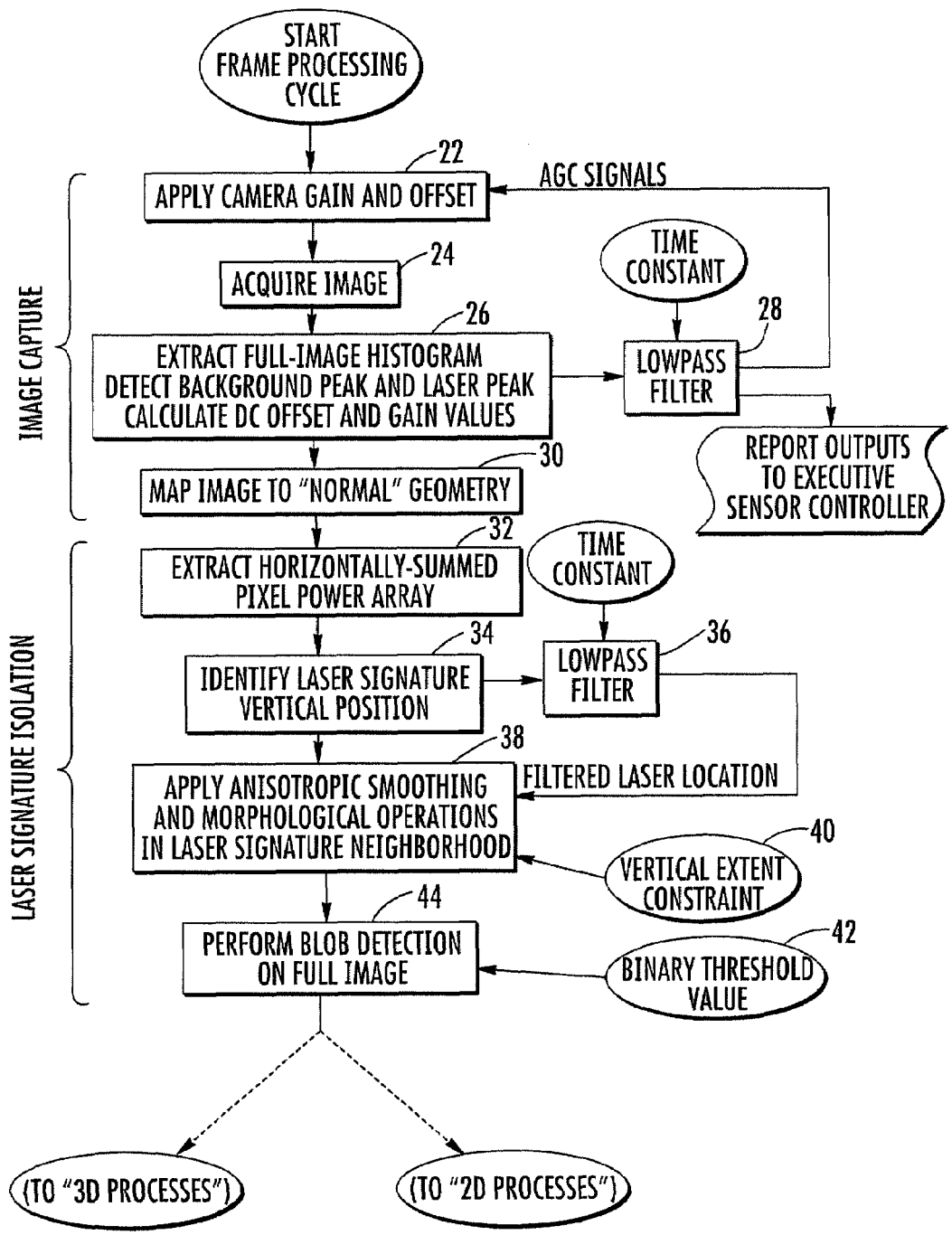
FIG. 4 is a flowchart illustrating pre-processes for inspecting a workpiece according to one embodiment of the present invention.

FIG. 4 illustrates the general image processing steps which are undertaken before the 2D (FIG. 5) and 3D (FIG. 6) processes are executed independently. Two actions occur in succession, beginning with the actual acquisition of image data from the camera 12 and followed by the isolation and pre-processing of the portion of the image containing the laser signature 30.

Not indicated in FIG. 4 are the static calibrations that take place when first setting up the camera 12. For example, the static calibrations may include setting the lens focus and aperture to nominal values and determining the pixels per inch at various locations over the operational depth of field. This latter goes into a table or second-order function relating pixel size to vertical location within the image for the purpose of accurately measuring any detected features. Another potential static calibration step is to store the path of the laser signature 30 that matches a flat surface by placing a test coupon below the camera 12 and recording the signature shape. This may be later subtracted from the dynamic laser signature, in each laser frame, to obtain the deviation from a flat surface.

With reference to FIG. 4, the image capture aspect includes setting the camera gain and DC offset (block 22) according to the output of a lowpass filter. These control settings are derived from a lowpass filter with a large time constant in order to slow the reaction to the occasional absence of a laser signature, large changes of background appearance due to repositioning the camera 12 away from the workpiece, or sudden changes in area lighting level. The signals involved in this calibration are output, such as in an executive data report, so that the executive controller 19 may make a determination of sensor image validity, i.e., to make an independent evaluation of whether a given image frame is actually viewing a valid workpiece. Once the gain and offset are set, an image of the workpiece is acquired (block 24), and the camera 12 may sequentially acquire images as the workpiece 18 is moved.

A full-image power histogram is extracted from the image, and the probable intensity peaks of the background and of the laser signature are located (block 26). Correction signals to the camera DC offset and gain are calculated to move the background power level into the lower 25% of the histogram and push the laser signature power level into the upper 95%. The lowpass filter inputs may be updated (block 28) with these corrections to be used in determining the gain and offset for acquiring additional images.

The image is mapped to a geometry (block 30) that removes perspective distortion, scales pixel sizes to represent square physical measurements, and orients the image to a standard position for analysis by the processing algorithms. This is done by applying geometric image warping and mapping (e.g., flipping the image vertically) using parameters that have been predetermined by the physical mounting orientation of the camera 12. The correct orientation results in the laser signature line placed horizontally across the image (parallel to pixel rows) and near the center at a nominal range.

With respect to the laser signature isolation aspect of FIG. 4, a horizontally-summed histogram is extracted by adding up all power in each row of the image pixels (block 32). The probable vertical location of the laser signature is identified by locating the largest peak in the horizontal summation histogram and verifying that the immediate neighborhood of the peak has a generally-Gaussian shape (block 34). If the neighborhood of the peak is not generally-Gaussian in shape, then the identified peak is not the probable vertical location of the laser signature. The laser signature location is taken to be the image row number of this peak. The location value is forwarded to a lowpass filter with a time constant sufficiently large so as to prevent overreacting to single-image noise events (block 36).

Using the output of this lowpass filter, which forms a "smoothed" laser signature location, various image filtering operations are performed within the local vertical neighborhood of the signature (block 38). These operations are intended to compensate for "noisy" laser line appearance (primarily caused by the globular nature of the composite resin surface, but also including to an extent the normal "speckle" associated with monochromatic light), and may include isotropic or anisotropic smoothing and gray morphological opening or closing operations. The pixel extent of the local vertical neighborhood (i.e., region of interest vertically of the laser signature) is a control parameter which may or may not be calculated dynamically by another process (block 40).

Using an intensity threshold level (block 42), which may be calculated by a function of the specific shape of the intensity distribution of the background tape material or set as a constant, all bright, contiguous objects within the image frame are identified and separated out ("segmented") in order to perform binary blob detection on the full image (block 44). In a similar manner and using a different threshold, all the dark, contiguous objects within the image frame are segmented. Contiguous features that are identified by a segmentation process involving a binary threshold are known to those or ordinary skill in the machine vision and image processing industry as "binary objects" or "blobs." Typically, a laser signature will include several bright spots or blobs.

Figure 5:
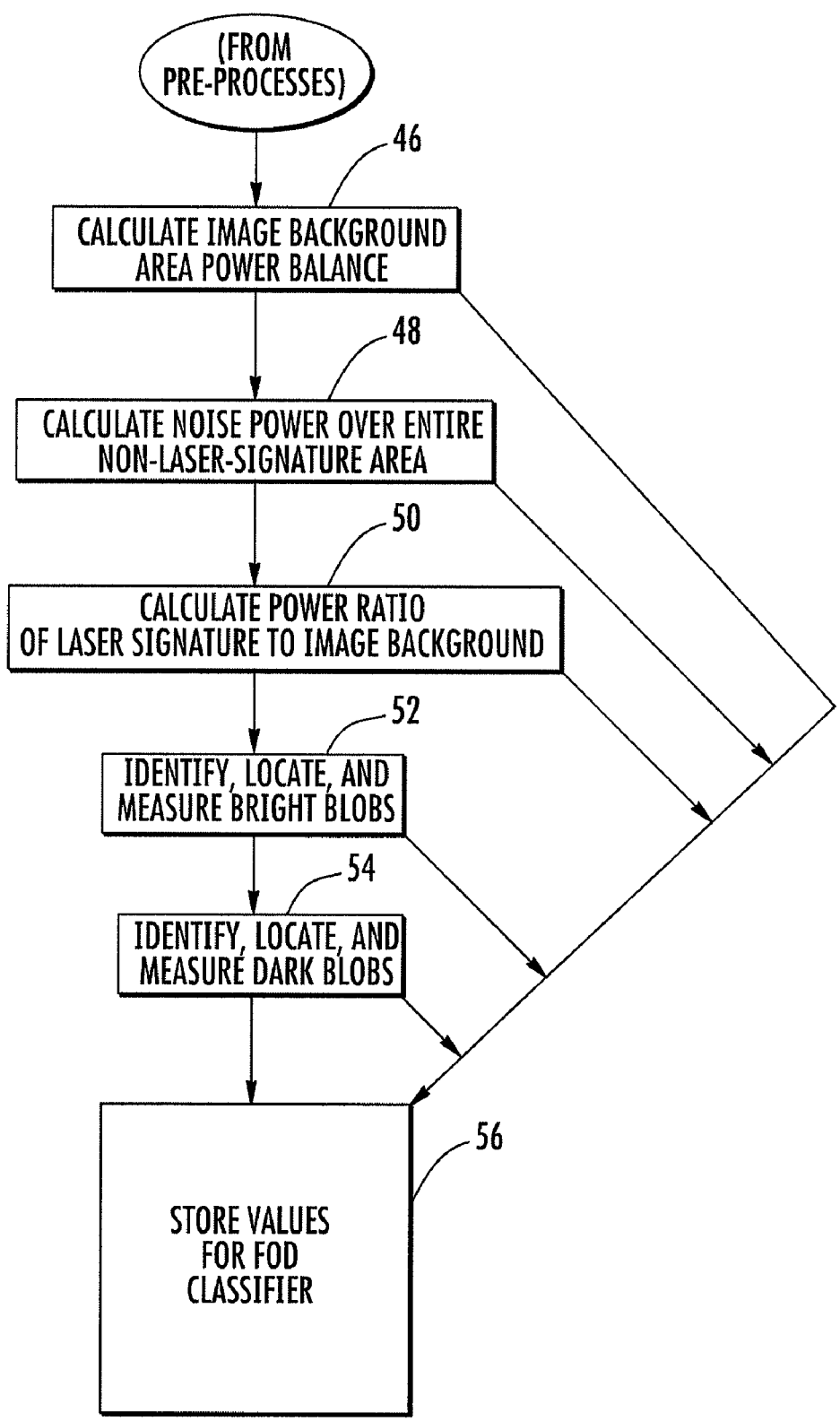
FIG. 5 is a flowchart illustrating two-dimensional processes for inspecting a workpiece according to one embodiment of the present invention.

Various signals derived using the algorithms set forth in FIG. 4, such as the two lists of bright and dark objects, are used as input into the 2D and 3D processes. FIG. 5 illustrates steps for performing 2D analysis according to one embodiment of the present invention. The relevant portions of the acquired image include the portions above and below the laser signature region that was previously defined by the laser neighborhood vertical extent. All regions (including the laser signature area) include the entire width of the image. For the purposes of this discussion, the areas above the laser signature line, the laser signature line, and below the laser signature line will be referred to as, respectively from the top to the bottom of the image, as the "upper," "laser," and "lower" areas. Signals extracted using processes set forth in FIG. 5 are forwarded to the foreign object debris (FOD) classifier discussed in conjunction with FIG. 8, which uses the signals to identify and measure any FOD found on the workpiece and represented in the image. However, the output of the 2D processes is not used to locate tape or tow joints on the workpiece.

With reference to FIG. 5, the normalized image background power is calculated by summing all pixel values independently for the upper and lower regions, and producing a measurement of the relationship between the regions, which may be a simple ratio or a more complex rule-based function that switches among various statistical measures and/or weights, based on total intensity (block 46). The normalized background image noise power is calculated collectively over both the upper and lower regions, which is defined as the standard deviation of all pixel values in the image that do not represent the laser signature (block 48). Then, a normalized ratio of the laser signature power to the sum of the background image power is calculated in both the upper and lower regions (block 50). Using the bright blob list developed in the pre-processing phase (see FIG. 4), large coherent bright blobs away from the laser are identified (implies a surface object such as backing paper), and the size, shape, total power, and/or location of the bright blobs are sent to the FOD classifier (block 52). Similarly, using the dark blob list developed in the pre-processing phase (see FIG. 4), large coherent dark spots away from the laser are located (implies a surface object such as plastic film), and the size, shape, total power, and/or location of the dark blobs are sent to the FOD classifier (block 54). The values identified for the bright and dark blobs are then stored to facilitate the classification of FOD (block 56) (see FIG. 8).

Figure 6:
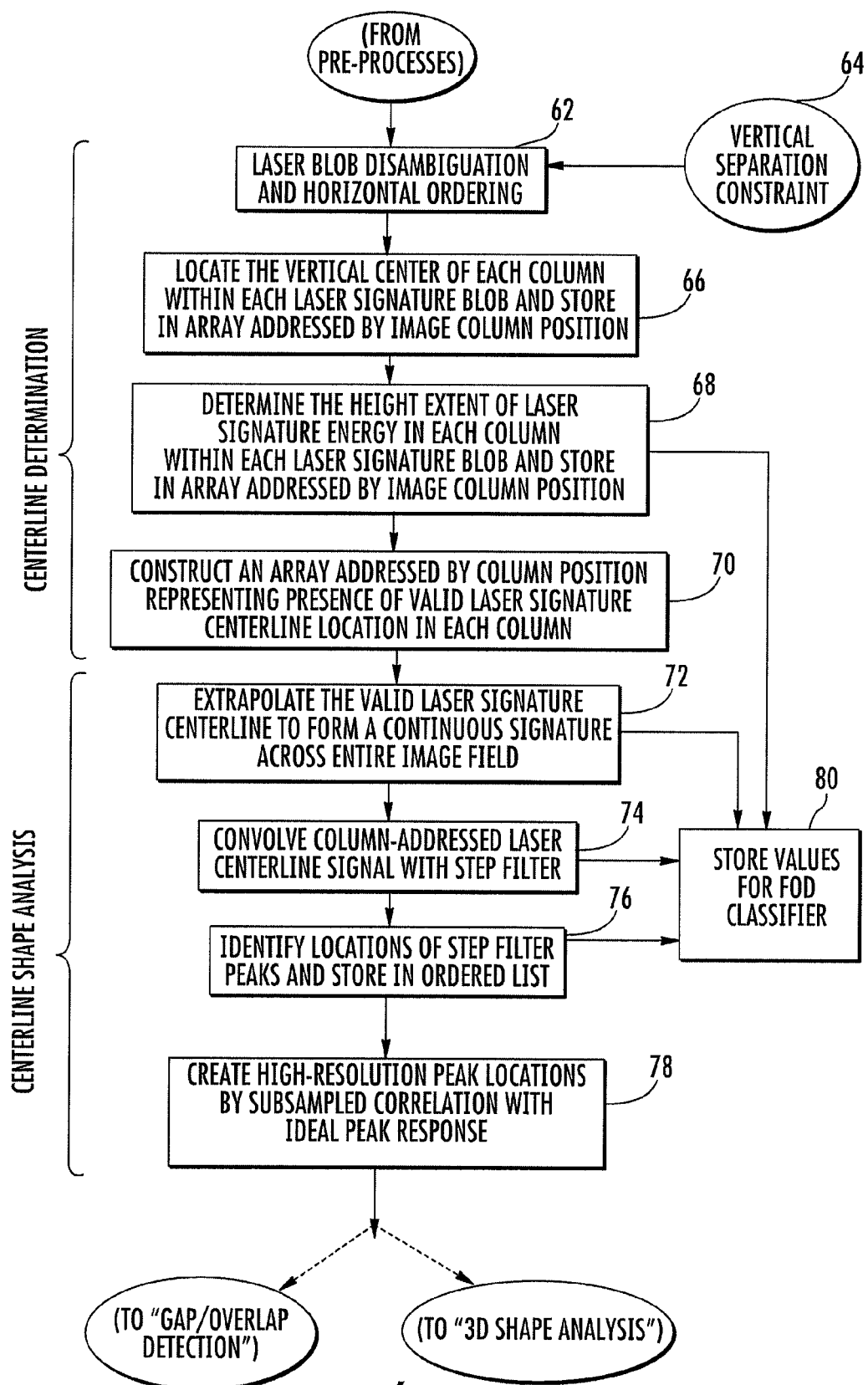
FIG. 6 is a flowchart illustrating three-dimensional processes for inspecting a workpiece according to one embodiment of the present invention.

FIG. 6 illustrates a method for performing 3D processes on an acquired image according to one embodiment of the present invention. The 3D processes include two aspects for extracting and storing the image of the laser line signature: an estimate of the vertical location of the centerline of the laser line signature, and the vertical extent (i.e., width) of the laser line signature at each column of the overall image. An array is generated that indicates the presence or absence of the laser line signature for each column in order to identify breaks in the line which may be caused by FOD that has some degree of height associated with it. The 2D and 3D processes may be performed simultaneously in a multi-threaded or multi-processor computing architecture.

Figure 12:
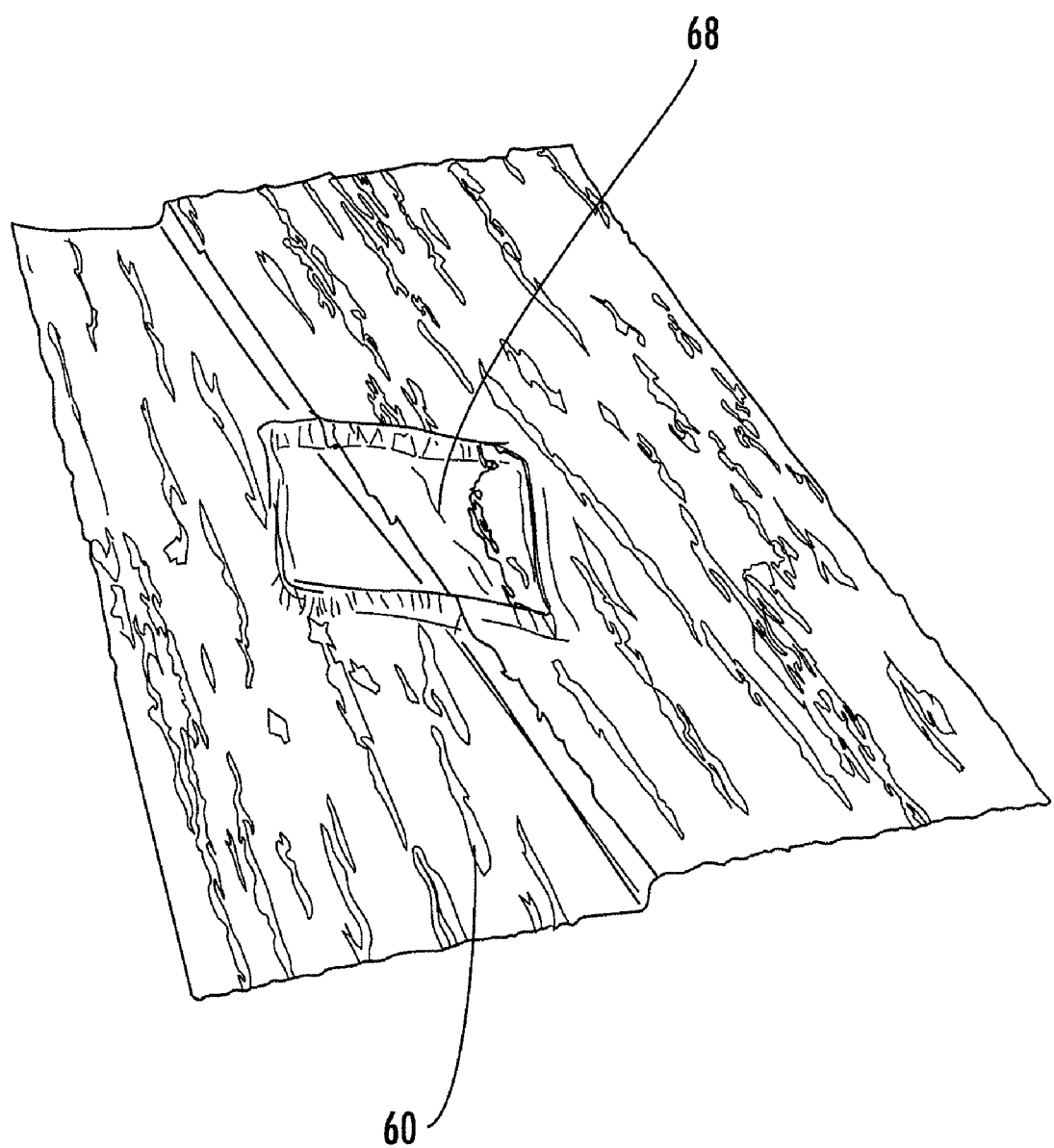
Figure 13:
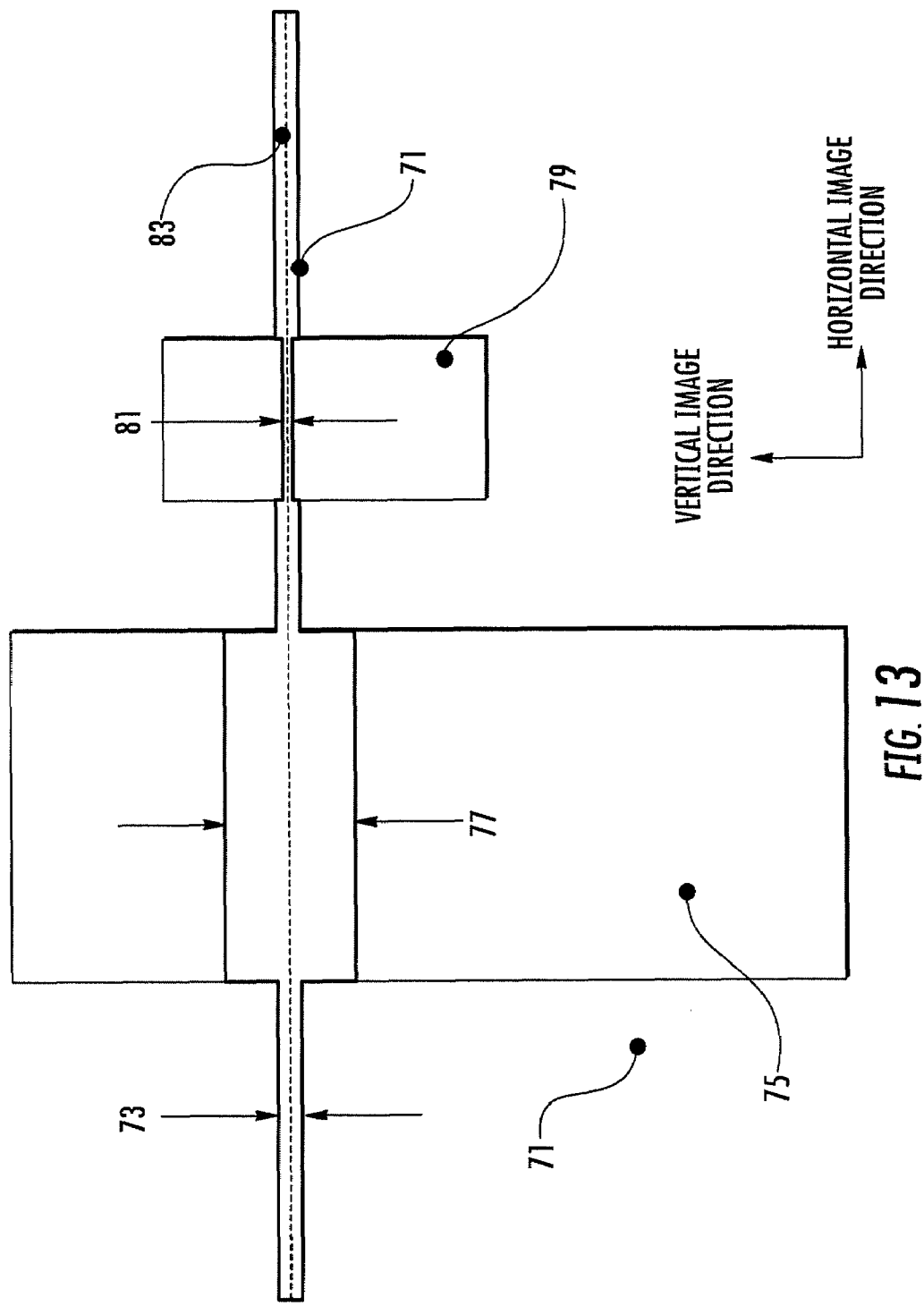
FIG. 13 illustrates a vertical extent of a laser signature for various workpieces according to one embodiment of the present invention.

The "vertical extent" of the horizontal laser line may be defined as simply its width, as though it were painted by a brush with varying degrees of pressure (see FIG. 13). Because the gain and DC offset of the camera are controlled to place the laser blobs near the maximum brightness to which the camera is normally exposed, any material that reflects a greater amount of light energy than the normal composite surface will overexpose the camera and produce a "fat" line. This is also known as "blooming" to those of ordinary skill in the video industry art. Normally, blooming is avoided, but due to the nature of the 3D processes, blooming is utilized to broaden the amount of information gathered about the surface of the workpiece. Indeed, the "fatness" of the laser line signature is used to recognize some of the FOD types the camera is required to detect. For example, FIG. 12 illustrates a square bit of FOD material 58 (backing tape) on top of a crossing edge of composite tape 60. In the false-color image, the width of the laser line signature may be coded by blue color intensity. The 3D appearance of the surface is created by successive laser signature centerlines, as explained below.

Referring to FIG. 6, laser signature blobs are disambiguated from potential FOD objects by disassociating "disconnected" blobs from the laser signature according to the location, size, and width-to-height ratio of the blobs (block 62). Blobs that are completely contained within a certain vertical range or radial separation (block 64), closely related to the vertical neighborhood size that defines the "laser" region, close to each other horizontally based on distance represented by number of pixels using an empirically derived value, and exhibit a large width-to-height aspect ratio are classified as "laser blobs." All other objects are classified as "FOD blobs."

For each laser blob, the vertical center point within each single column is located to determine the apparent location of the "centerline" of the laser signature (block 66). Locating the vertical center point may be done in two ways, depending on certain other signals extracted from the overall image a) by using the gray center of mass (an industry-standard method), or b) by averaging the vertical locations where the brightness crosses one or more binary threshold boundaries. The values indicative of the vertical locations are placed into an array that has a number of elements equal to the complete horizontal extent of the camera image in pixels.

In a similar manner, the vertical width (i.e., extent of the bright pixels in the vertical image direction) of the laser blob in each column is measured and stored (block 68). Alternatively, the half-width of the gray peak may be used. This is a signal that is related to surface specularity as discussed above. This vertical width is forwarded to the FOD classifier (block 80) (see FIG. 8). A TRUE/FALSE array is constructed that is addressed by column position and represents the existence of a valid laser signature at a centerline location at each column (block 70). The array is used in subsequent processing steps to ensure that the data is actual signature data rather than extrapolated data.

It should be noted, as shown in FIG. 13, that both wider and narrower laser line widths are of interest, the former implying that (at the angle between the camera's 12 optical axis and the illumination source 14) the surface of a workpiece appears to be highly reflective, and the latter implying the opposite. For example, in FIG. 13, a "normal" composite material 71 reflects an average width of laser line signature 73, whereas a bright material such as backing paper 75 reflects a wide signature 77 due to ordinary camera blooming. A dark or transparent material 79 such as tape or mylar film returns very little light to the camera thus producing a very narrow laser line 81. Thus, in addition to measuring the vertical width of an object above the working surface, the reflectivity of the object can be determined. Note that the location of the laser centerline 83 is unchanged by thin contaminants of little or no physical height.

Any disconnected blobs presumed to be along the laser signature are connected with a straight line from the edges of adjacent laser blob centerlines (block 72). This is a neighborhood operation constrained by an empirically derived maximum pixel separation value such that discontinuities above a certain length constitute a "broken line." These discontinuities are indicative of FOD such as a piece of debris obstructing the laser fan beam, or an actual hole in the surface of the workpiece. The locations and size of the discontinuities are forwarded to the FOD classifier for further processing (block 80) (see FIG. 8). Gaps in the workpiece that are within an empirically derived acceptable tolerance are filled in with a smooth function in order to avoid throwing the edge detection filter off if a step is detected in the workpiece near such a gap. The smoothing function could be mechanized in the detection filter itself, but may be incapable of performing at the same processing speeds.

As used herein, the empirically derived constants and/or parameters are not universal but, instead, are dependent upon the nature of the application of particular aspects of the present invention. For example, these values may be determined within the context of local machine lighting, vibration levels, and the particular workpiece reflectivity and specularity functions so as to adjust the operational robustness for a given environment.

The laser signature centerline exhibits sharp steps where an edge exists that runs lengthwise down the workpiece, such as the side of a tape being applied during a manufacturing procedure. Mathematically, these are reliably detected by convolving the laser centerline as a function of the image width with a step filter kernel (block 74). This kernel, of some width (number of elements), has the value of −1 for the first half of its elements, and +1 for its second half. Note that the width of the filter allows for noise reduction by simple averaging, but also trades off this value against poorer detection of closely-spaced steps (such as would be found where only a small gap exists between adjacent composite tape). The step filter is convolved with the entire laser centerline array to produce an array of filter power output values. This array is forwarded to the "Shape Analysis" processes (see FIG. 9), that is used to create pseudo-3D topological maps of the workpiece surface. The maximum and minimum peak power values (the output of the filter is bipolar) may be latched and forwarded to the FOD classifier (block 80) (see FIG. 8).

The peaks of the step filter output may then be located (block 76), where a positive value indicates a step "down," and a negative value indicates a step "up." The locations of these sections are checked against the validity array, so as to disallow any edge detections that may creep into regions of no information. A list of peak locations is created and ordered by magnitude of the filter response for further processing. The total number of peaks are stored and forwarded to the FOD classifier (block 80).

A "perfect" step in the laser centerline array, processed by the step filter, will have an output resembling a triangle. A higher-resolution, cross-correlation with a triangle function is applied to each detected peak in order to measure the "best fit" location of the maximum output (block 78). The cross-correlation provides some degree of sub-pixel resolution because multiple pixels are used to arrive at a single measurement. The cross-correlation is typically separated from the first step filter convolution because it is done at higher resolution and thus requires more computation. Normally, the step filter kernel could be convolved with the triangle kernel to create one function with which to multiply the entire centerline array; however, the step filter and triangle kernels would both have to be of the same or higher sampling resolution. Since steps are relatively rare across the image, the method described here speeds up the overall operation significantly.

Figure 7:
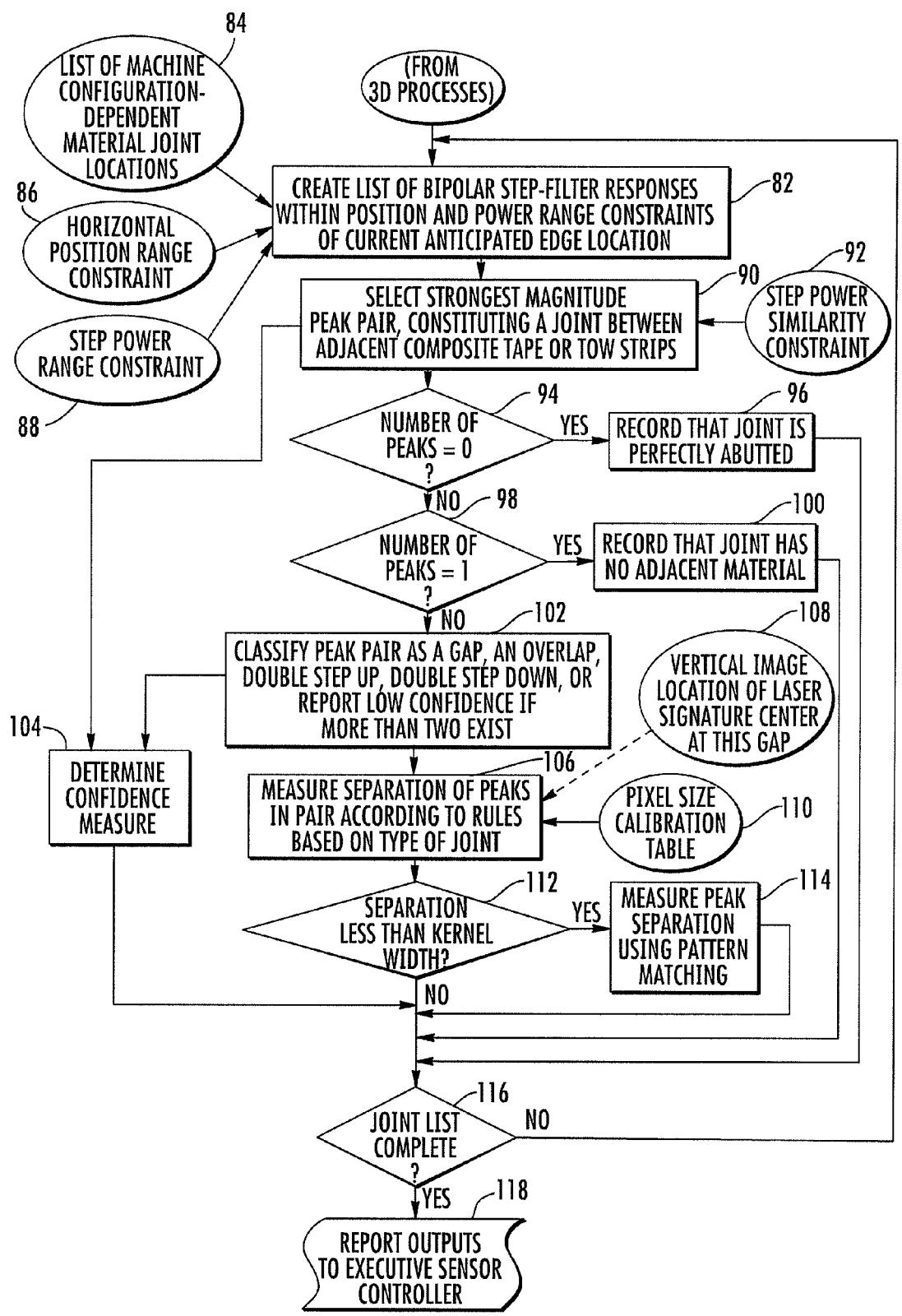
FIG. 7 is a flowchart illustrating processes for identifying features for inspecting a workpiece according to one embodiment of the present invention.

FIG. 7 illustrates a method for identifying features associated with composite tape or tow strips according to an embodiment of the present invention. The objective of FIG. 7 is to identify features, such as edges of composite tape or tow strips close to their expected locations, and determine if two edges butted together (i.e., a joint) are separated by a gap, overlap each other, or exhibit some unusual characteristic that implies a problem.

The method of FIG. 7 generally includes semantically collecting information for identifying features associated with the workpiece 18 and performing pixel-dependent functions on the laser line signature 30. In particular, the inputs to the first portion of the process (i.e., detection) include an expected set of horizontal locations of tape or tow joints for this region of the workpiece, which may be set externally by the executive controller 19 since the composite fabrication machine might change this dynamically, a list of step feature locations along the laser centerline curve represented by filter peaks calculated in the previous 3D analysis, and the constraint parameters on expected maximum and minimum peak powers. For the second portion of the process, once gaps or overlaps have been semantically identified, measurement of the spacing requires knowledge of the vertical location of the laser signature in order to correctly apply the pixel size calibration for that region of the image.

Referring to FIG. 7, a magnitude-ordered list of gaps that lie within the expected range of the joint location is created (block 82). In particular, a list of machine configuration-dependent material joint locations are provided (block 84), and a list of bipolar step-filter responses within the horizontal position constraint window (block 86) and power-range constraints (block 88) of the anticipated edge location are created. For a step peak to be a "valid" potential candidate for membership in a joint, it must also fall within an anticipated broad range of power magnitude. This list may contain any number of elements but practically, the anticipated number is zero (the joint is perfectly butted together) or two (a simple gap or overlap exists).

The pair of peaks of the largest magnitude within this list are identified and compared to verify that they both inhabit the same range constraint window (block 90). The pair of peaks are further examined to verify that they are close to each other in relative power, which is a smaller range than the power range mentioned in the previous paragraph (block 92). This essentially asks the question, "are these two peaks sufficiently similar that they may be construed as the two sides of a gap or overlap?" If there are no peaks within the range of acceptable levels (block 94), then the conclusion is that the joint is abutted perfectly (block 96) and further processing of this joint is skipped. If there exists only one peak of acceptable level (block 98), the conclusion is that this is not a joint, but the edge of a single piece of tape or tow (i.e., there is no adjacent tape or tow) (block 100).

If the number of peaks of acceptable magnitude is exactly two, the pair is classified according to the step polarity as one of a "gap" (a step down followed by a step up), an "overlap" (a step up followed by a step down), or an unknown, unusual condition (two steps up or two steps down) (block 102). If an unknown, unusual condition is found, a confidence value may be used to disambiguate gaps or overlaps (block 104)

Certain measures or signals of the population of list elements are used to determine a confidence value for the eventual joint measurement (block 104). Example signals which call into question the validity of a given joint identification include (from block 90) too wide a variance of edge peak powers, any very large edges (may indicate material that has become unstuck to the substrate) or too many edges, and (from block 102) a closely-spaced series of steps of the same polarity.

If a gap or an overlap is positively-identified, the separation of peaks in the pair of peaks is measured based on the type of joint (block 106). In particular, using the vertical image location of the laser signature center at the gap or overlap, the width of the gap or overlap is measured by subtracting the high-resolution distance between the peaks and converting to the required units through the use of a pixel size calibration mechanism (block 110) that uses the vertical location of the steps in the image. Depending upon the geometry of the sensor for a given application, this correction may be as simple as a table or as complex as a multi-dimensional topological function. If the joint represents an overlap of material, an additional offset is applied using an empirically determined factor to account for the unsharp nature of the overlapped edges.

The separation width of the filter kernel width is determined (block 112), and if there are gaps or overlaps that are less than half the filter kernel width, the gaps or overlaps are degraded (the step detector output is less sensitive), and a pattern-matching method for measurement of width is employed (block 114). Pattern matching correlates a series of pulse-shaped patterns with the center location of the joint rather than simply subtracting two step-filter peak locations. The best match is chosen to represent the width of the actual joint signature.

The above-described steps are performed for each joint in the joint list (i.e., gap or overlap) (block 116). A data report may be created and provided to the external executive controller 19 (block 118), which contains the semantic description of all of the joints within the sensor field of view, the widths of any gaps or overlaps present, the absence of any expected tape or tow, and the confidence values for each of these conclusions.

Figure 8:
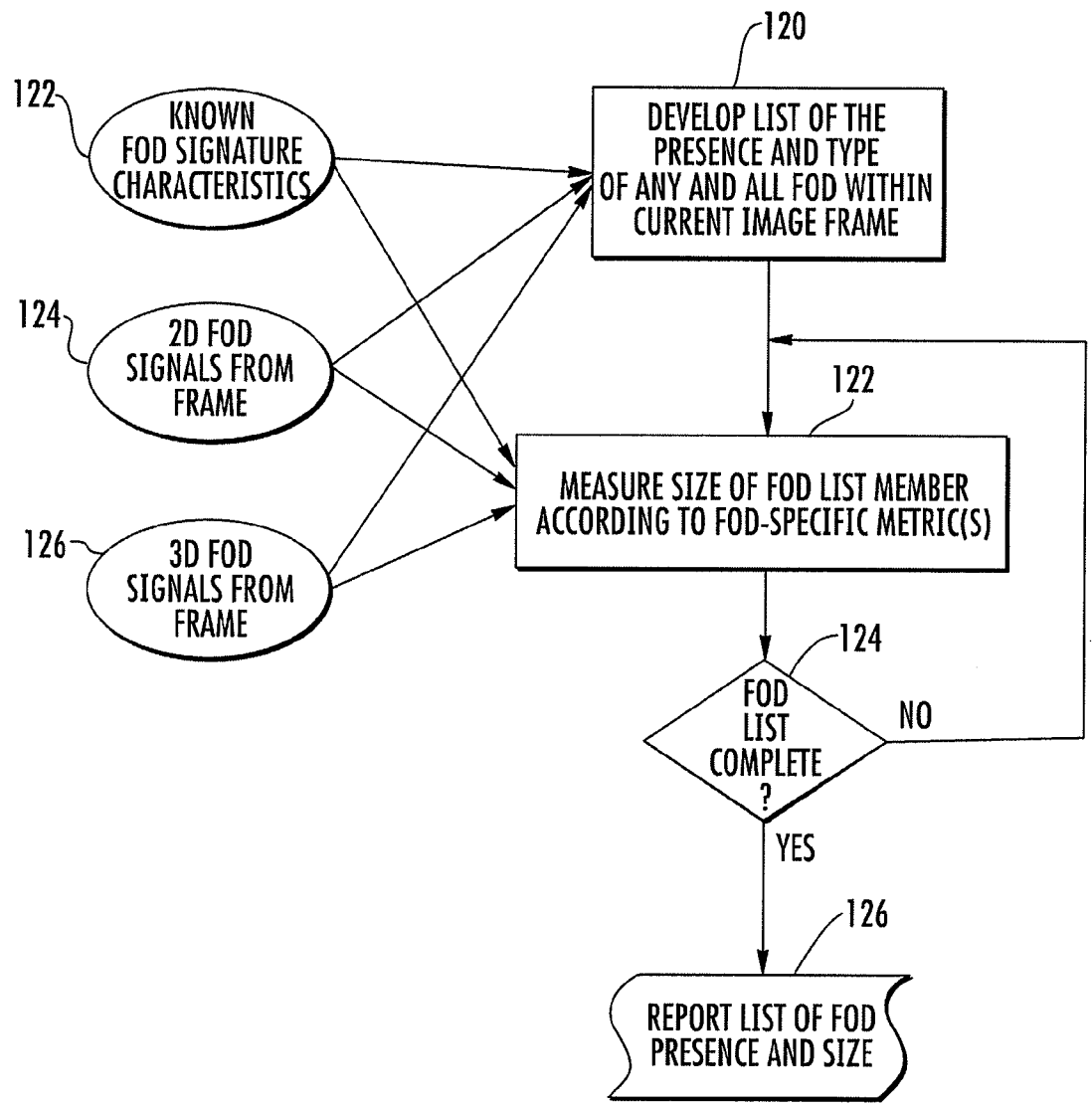
FIG. 8 is a flowchart illustrating processes for classifying features for inspecting a workpiece according to one embodiment of the present invention.

FIG. 8 depicts a method for classifying features (e.g., FOD) associated with a workpiece according to one embodiment of the present invention. In general, FOD classification utilizes outputs from both the 2D analysis and 3D analysis described in conjunction with FIGS. 5 and 6, respectively, in combination with a database of known FOD characteristics. Typically, the classification does not execute until both the 2D and 3D inputs are available. Any given image may contain any number of types of FOD that are arranged in any spatial relationship to the frame and may or may not physically overlap one another.

Referring to FIG. 8, the first step of FOD classification is to build a list of potential discrete FOD signatures in the image frame (block 120) based on known FOD signal characteristics (block 122), signals that were developed during the 2D image processing phase (block 124), and signals that were developed during the 3D processing phase (block 126). Signals are related to probable FOD presence by a table of rules. In particular, the logic looks for matches between known FOD characteristics and sets of signal levels that exist within the image. A matching rule may take the form of simple thresholds in combination, e.g., that the upper area background power must be above a level $P_U$, and the lower area background must be below a level $P_L$ or dynamic combinatorial relationships, e.g., the laser signature power must be some percentage greater than the sum of the upper and lower background power levels. Additionally, in some cases the rule may be a simple truth function, such as the presence of two closely-spaced edge steps in the laser signature that displace the surface in the same direction, which may indicate the presence of features such as a wrinkle or other similar surface inconsistency. Moreover, the signal confidence values calculated with respect to FIG. 7 may be used to disambiguate the FOD types by selecting the type that has the overall highest confidence level.

Each type of FOD may have a unique method of measuring its extent in order to determine compliance of the workpiece under the image to the engineering specifications (block 122). For example, if a FOD signature indicates that the inconsistency consists of a "resin ball," the specification may require that it be less than a certain diameter in the plane of the surface and below a certain height above it, whereas if the FOD is identified as a piece of backing paper it may have a certain allowable width and length, but no height restriction (since it is essentially 2D). Thus, the FOD classifier also uses the known characteristics of each FOD type to select a method of measurement and then to determine the dimensions of each entry in the list of inconsistencies in the image frame. These measurements are not necessarily limited to physical dimensions, but may also include such metrics as roughness or reflective power. Once the entire list of FOD objects is processed for the frame (block 124), a data report is formatted and sent to the external executive controller 19 (block 126).

Figure 9:
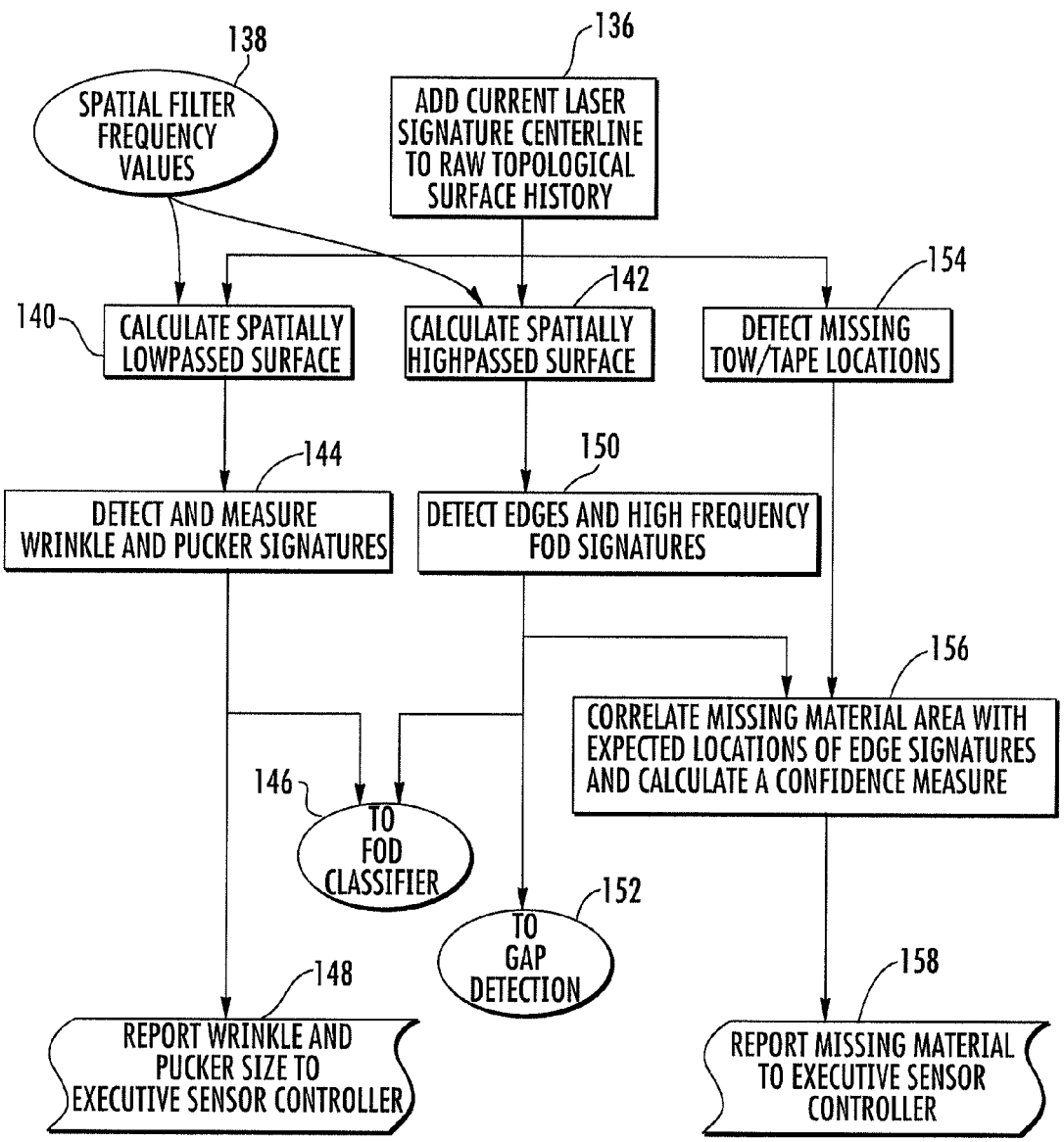
FIG. 9 is a flowchart illustrating processes for analyzing three-dimensional features for inspecting a workpiece according to one embodiment of the present invention.

FIG. 9 illustrates a method for analyzing the shape of the laser line signature according to one embodiment of the present invention. The shape analysis is a "meta" process in the sense that it involves information over a large number of image frames. In addition, the shape analysis process operates upon a topological surface devised by stacking laser signature centerlines together, wherein the "width" of the surface is directly the image width (in pixels), the "length" of the surface represents time (each slice coming from one image frame), and the "depth" of the surface is the deviation of the image vertical location of each centerline pixel from the flat surface line determined during static calibration before the camera is used.

Figure 10:
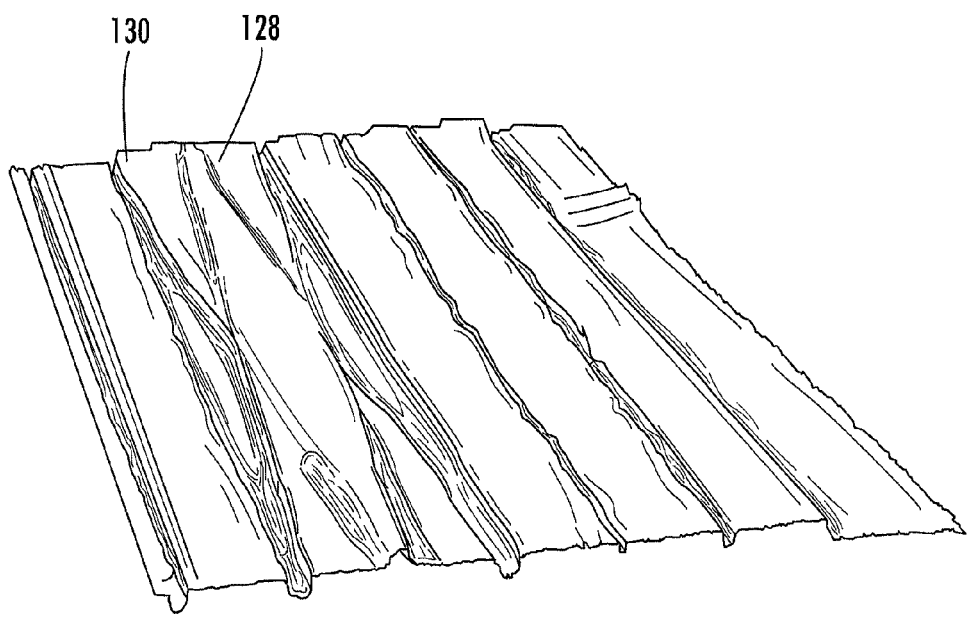
FIGS. 10-12 depict topological images of features on a workpiece generated with an inspection system according to an embodiment of the present invention.

FIG. 10 illustrates an exemplary topological surface created from a series of laser signature centerline arrays. The topological surface includes a section of a continuously-laid group of six adjacent tow strips being laid upon a mandrel in the direction seen in the image from front to rear. The $3^{rd}$ from the left tow 128 crosses the $2^{nd}$ from the left tow 130 in this interval. In this particular false-color representation, edges that "step down" from left-to-right may be tinted green, and edges that "step up" from left-to-right may be tinted red (color intensity is proportional to the size and sharpness of the step). The blue color channel may be used in proportion to laser line width as described above with respect to FIG. 12. The step heights evident in the image are the thickness of this particular tow material, which is approximately 0.008 inch, and has been exaggerated for this representation.

With reference to FIG. 9, the raw topological surface is updated by adding the current laser signature centerline thereto (block 136). The surface data contains pseudo-3D information, as described previously, as well as the width of the laser line signature that is a function of the composite material reflectivity. Using spatial filter frequency values (block 138), which may be predefined constants determined by engineering specifications for differentiating features, two other surfaces that are spatially filtered are calculated from the raw surface to separate out low spatial frequency features (block 140), e.g. wrinkles and tape puckers, and high spatial frequency features (block 142), e.g. tape edges and discrete FOD objects. Any wrinkle and pucker signatures that are currently found on the low frequency surface are detected and measured (block 144). The measurements include the 2D outline of the feature upon the nominally-flat surface of the workpiece, the maximum height above it, and a measure of the volume between the actual and nominal surfaces.

Instances of such features are collected in a list, which may change with every image frame and be forwarded as an input to the FOD classifier routine described earlier (block 146). A report of any wrinkle or pucker events that are completed may be provided to the executive controller 19 (block 148). A completed event typically occurs when the composite material has returned to the nominal condition, and a discrete wrinkle or pucker "object" can be identified and measured for inclusion within the report.

From the high spatial frequency surface, any instances of tape or tow material edges and FOD may be detected (block 150), which is qualitatively and quantitatively different from the previously-described algorithms (see FIG. 7) that are running on each independent image frame. A semantic list of edges and/or FOD are created and forwarded to both the FOD classifier (block 146) (see FIG. 8) and to the gap detection processes (block 152) (see FIG. 7), where the information will be combined with the framewise-instantaneous information to develop improved classifications of these objects.

From the raw topological surface, when operating the system 10 on a tow-based manufacturing process, the presence of missing tows is detected by using a spatial pattern-matching technique that is matched with the known tow dimensions (block 154). If one or more missing tows are detected, the missing tows are compared with the expected relevant edges found in the high spatial frequency image for verification. A confidence value regarding the missing tows may also be calculated. A report of missing tows may be formatted and transmitted to the executive sensor controller (block 158). The topological surfaces may also optionally be presented to an operator as a 3D display similar to that shown in FIGS. 10 and 11 when a viewpoint is desired. There are many techniques for presenting the views of the topological surfaces, such as in a static, single-snapshot offline reconstruction.

According to one aspect of the present invention, the system generally operates under control of a computer program product. The computer program product for performing the methods of embodiments of the present invention includes a computer-readable storage medium, such as the memory device associated with a processing element, and computer-readable program code portions, such as a series of computer instructions, embodied in the computer-readable storage medium.

In this regard, FIGS. 4-9 are control flow diagrams of methods and program products according to the invention. It will be understood that each block or step of the control flow diagrams, and combinations of blocks in the control flow diagrams, can be implemented by computer program instructions. These computer program instructions may be loaded onto a processing element, such as a computer, server, or other programmable apparatus, to produce a machine, such that the instructions which execute on the processing element create means for implementing the functions specified in the block(s) or step(s) of the control flow diagrams. These computer program instructions may also be stored in a computer-readable memory that can direct the processing element to function in a particular manner, such that the instructions stored in the computer-readable memory produce an article of manufacture including instruction means which implement the function specified in the block(s) or step(s) of the control flow diagrams. The computer program instructions may also be loaded onto the processing element to cause a series of operational steps to be performed on the processing element to produce a computer implemented process such that the instructions which execute on the processing element provide steps for implementing the functions specified in the block(s) or step(s) of the control flow diagrams.

Accordingly, blocks or steps of the control flow diagrams support combinations of means for performing the specified functions, combinations of steps for performing the specified functions, and program instruction means for performing the specified functions. It will also be understood that each block or step of the control flow diagrams, and combinations of blocks or steps in the control flow diagrams, can be implemented by special purpose hardware-based computer systems which perform the specified functions or steps, or combinations of special purpose hardware and computer instructions.

Thus, embodiments of the present invention may provide several advantages. For example, the data system 16 is capable of analyzing images to provide both 2D and 3D information indicative of a workpiece 18. In addition, the system 10 utilizes a fan beam having a shallow incidence angle that is configured to detect specific features of a workpiece to improve the accuracy of identifying the same, as well as identifying surface debris in order to differentiate actual features from common structures associated with the workpiece (e.g., ridge-like structures in the central regions of composite tape material). Moreover, the system 10 is capable of inspecting the workpiece 18 during processing and in real time, which may reduce down time and increase efficiency. Thus, the system 10 provides a hybrid of 2D and 3D information by analyzing a laser line signature 30 in order to inspect workpieces 18 having various surface configurations in a single image frame interval. Furthermore, embodiments of the present invention implement algorithms to analyze noisy laser line signatures produced both by motion blur and out-of-focused conditions, track signatures during motion through successive image frames, and recognize small discontinuous line changes on curved lines in the presence of noisy image power. In addition, aspects of the present invention utilize a rule-based system to classify surface debris (FOD) using a mapped combination of 2D and pseudo-3D characteristics, in order to satisfy manufacturing specifications that vary according to the exact type of feature associated with the workpiece, wherein primitive measures (i.e., not controlled by what the system observes) derived from various algorithms are mapped to, and associated with, signature characteristics of the various known forms of features.

Many modifications and other embodiments of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for inspecting a workplace comprising:
   illuminating at least a portion of the workpiece with at least one illumination beam;
   capturing at least one image comprising at least one line signature formed by illuminating the workpiece with the illumination beam;
   independently performing two-dimensional and three-dimensional processes on the captured image; and
   classifying at least one feature associated with the workpiece based at least in part on data generated by the two-dimensional and three-dimensional processes.

2. The method according to claim 1, further comprising performing a manufacturing process on a moving workpiece during the illuminating and capturing steps.

3. The method according to claim 1, wherein illuminating comprises illuminating the workpiece with the illumination beam at an oblique incidence angle relative to the workpiece.

4. The method according to claim 1, wherein classifying comprises classifying a foreign object debris associated with the workpiece.

5. The method according to claim 1, wherein capturing comprises capturing at least one image comprising at least a background and the line signature illuminated on the workpiece.

6. The method according to claim 5, further comprising isolating the line signature from the background captured on the image.

7. The method according to claim 6, further comprising generating a power histogram of the background and line signature.

8. The method according to claim 7, further comprising determining a vertical location of the line signature based on the power histogram.

9. The method according to claim 5, wherein performing two-dimensional processes comprises calculating at least one of an image background power, a background image noise power, and a power ratio of the illumination beam to the background.

10. The method according to claim 1, further comprising identifying bright and dark contiguous objects on the captured image using an intensity threshold level.

11. The method according to claim 10, wherein performing two-dimensional processes comprises determining at least one of size, shape, total power, and location of each of the bright and dark contiguous objects.

12. The method according to claim 10, wherein performing three-dimensional processes comprises disassociating the bright and dark contiguous objects associated with the line signature from those bright and dark contiguous objects not associated with the line signature.

13. The method according to claim 12, wherein performing three-dimensional processes comprises determining a location of a centerline and an extent of each column representative of the disassociated bright and dark contiguous objects.

14. The method according to claim 13, wherein performing three-dimensional processes comprises extrapolating an aggregate centerline representative of a centerline of the line signature based on each of the centerlines determined for each of the disassociated bright and dark contiguous objects.

15. The method according to claim 14, wherein performing three-dimensional processes comprises convolving the aggregate centerline with a step filter kernel.

16. The method according to claim 15, wherein performing three-dimensional processes comprises locating peaks provided by the step filter kernel.

17. A method for inspecting a workpiece comprising:
illuminating at least a portion of the workpiece with at least one illumination beam;
capturing at least one image comprising at least one line signature formed by illuminating the workpiece with the illumination beam;
performing three-dimensional processes on the captured image, wherein the three-dimensional processes comprise determining at least one of a location of each line signature and an extent of at least a portion of each line signature; and
providing information indicative of at least one feature associated with the workpiece based on data generated by the three-dimensional processes.

18. The method of claim 17, wherein providing comprises providing at least one of information indicative of respective edges of the workpiece, a gap in the workpiece, an overlap on the workpiece, and a foreign object debris associated with the workpiece.

19. The method according to claim 17, further comprising identifying bright and dark contiguous objects on the captured image using an intensity threshold level.

20. The method according to claim 19, wherein performing three-dimensional processes comprises disassociating the bright and dark contiguous objects associated with the line signature from those bright and dark contiguous objects not associated with the line signature.

21. The method according to claim 20, wherein performing three-dimensional processes comprises determining a vertical location of a centerline of each line signature and a vertical extent of each column representative of the disassociated bright and dark contiguous objects.

22. The method according to claim 21, wherein performing three-dimensional processes comprises extrapolating an aggregate centerline representative of a centerline of the line signature based on each of the centerlines determined for each of the disassociated bright and dark contiguous objects.

23. The method according to claim 22, wherein performing three-dimensional processes comprises convolving the aggregate centerline with a step filter kernel.

24. The method according to claim 23, wherein performing three-dimensional processes comprises locating peaks provided by the step filter kernel.

25. The method according to claim 24, further comprising identifying at least one of a gap, an overlap, a double step up, and a double step down on the workpiece based at least in part on the number of peaks located by the step filter kernel.

26. The method according to claim 25, further comprising determining a width between a pair of peaks provided by the step filter kernel for each identified gap or overlap.

27. The method according to claim 17, further comprising calculating at least one of a low spatial frequency surface and a high spatial frequency surface associated with the workpiece based at least in part on data generated by the three-dimensional process.

28. The method according to claim 27, further comprising detecting at least one feature associated with the workpiece based at least in part on at least one of the low spatial frequency surface, the high spatial frequency surface, and the data generated by the three-dimensional process.

29. An apparatus for inspecting a workpiece comprising:
at least one illumination source positioned proximate to the workpiece and configured for illuminating at least a portion of the workpiece with at least one illumination beam;
at least one camera positioned proximate to the workpiece and configured for capturing at least one image comprising at least one line signature formed by illuminating the workpiece with the illumination beam;
a data system capable of independently performing two-dimensional and three-dimensional processes on the captured image and classifying at least one feature associated with the workpiece based at least in part on data generated by the two-dimensional and three- dimensional processes.

30. The apparatus according to claim 29, wherein the at least one illumination source is configured for illuminating the workpiece with the illumination beam at an oblique incidence angle relative to the workpiece.

31. The apparatus according to claim 29, wherein the data system is capable of classifying a foreign object debris associated with the workpiece.

* * * * *